United States Patent
Billings et al.

(10) Patent No.: US 10,843,299 B2
(45) Date of Patent: *Nov. 24, 2020

(54) OBJECT RECOGNITION AND PRESENTATION FOR THE VISUALLY IMPAIRED

(71) Applicant: The Johns Hopkins University, Baltimore, MD (US)

(72) Inventors: Seth D. Billings, Bethesda, MD (US); Kapil D. Katyal, Chevy Chase, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/506,547

(22) Filed: Jul. 9, 2019

(65) Prior Publication Data

US 2019/0329364 A1    Oct. 31, 2019

Related U.S. Application Data

(63) Continuation-in-part of application No. 16/363,012, filed on Mar. 25, 2019, now Pat. No. 10,646,966, (Continued)

(51) Int. Cl.
*G06K 9/00*    (2006.01)
*B23K 37/00*    (2006.01)
(Continued)

(52) U.S. Cl.
CPC ............ *B23K 37/006* (2013.01); *A61F 9/08* (2013.01); *B23K 9/167* (2013.01); *B23K 9/173* (2013.01);
(Continued)

(58) Field of Classification Search
CPC .......... B31D 5/0047; B31D 2205/0023; B31D 2205/0047; B31D 2205/0082;
(Continued)

(56) References Cited

U.S. PATENT DOCUMENTS 9,922,236 B2    3/2018    Moore et al.
10,265,218 B2    4/2019    Rollend et al.
(Continued)

OTHER PUBLICATIONS

P. Viola, et al., "Rapid Object Detection using a Boosted Cascade of Simple Features," Computer Vision and Pattern Recognition, 2001 (CVPR 2001), Proceedings of the 2001 IEEE Computer Society Conference, vol. 1. (2001), pp. I-511-I-518, 2001.
(Continued)

*Primary Examiner* — Tom Y Lu
(74) *Attorney, Agent, or Firm* — Todd R. Farnsworth

(57) ABSTRACT

An apparatus configured to perform object recognition is provided that includes a camera, an assistance feedback device, and processing circuitry. The processing circuitry may be configured to receive the plurality of images from the camera and repeatedly determine characteristic features within the plurality of images and compare the characteristic features within the plurality of images to an object identification dataset to determine object matches for identified objects within the plurality of images. The processing circuitry may be further configured to determine a name for identified objects from the object identification dataset, output, using the assistance feedback device, a position indicator for identified objects, and output the name of identified objects within the assistance feedback device field of view.

17 Claims, 13 Drawing Sheets

Related U.S. Application Data which is a continuation of application No. 15/671,696, filed on Aug. 8, 2017, now Pat. No. 10,265,218.

(60) Provisional application No. 62/695,959, filed on Jul. 10, 2018, provisional application No. 62/371,919, filed on Aug. 8, 2016.

(51) Int. Cl.

| | |
|---|---|
| *G06K 9/62* | (2006.01) |
| *A61F 9/08* | (2006.01) |
| *G06N 3/04* | (2006.01) |
| *H01R 13/648* | (2006.01) |
| *B23K 9/167* | (2006.01) |
| *H01R 13/22* | (2006.01) |
| *B23K 9/32* | (2006.01) |
| *B23K 9/173* | (2006.01) |
| *H01R 4/56* | (2006.01) |
| *H01R 13/24* | (2006.01) |

(52) U.S. Cl.
CPC ............ *B23K 9/32* (2013.01); *G06K 9/00671* (2013.01); *G06K 9/6202* (2013.01); *G06N 3/04* (2013.01); *H01R 13/22* (2013.01); *H01R 13/648* (2013.01); *G06N 3/0454* (2013.01); *H01R 4/56* (2013.01); *H01R 13/2421* (2013.01)

(58) Field of Classification Search
CPC .............. C09D 119/003; C09D 163/00; G02B 2027/0138; G02B 2027/014; G02B 2027/0178; G02B 27/017; G06F 3/005; G06F 3/016; G06F 3/167; G06F 19/00; G06F 19/3418; G06F 3/011; G06K 9/00201; G06K 9/00671; A61B 2560/0223; A61B 2562/0295; A61B 5/0022; A61B 5/14532; A61B 5/6898; A61B 5/7495; C08L 2666/02; C08L 2666/08; C12Q 1/54; G01N 33/66; Y10S 493/967

See application file for complete search history.

(56) References Cited

U.S. PATENT DOCUMENTS

| | | | |
|---|---|---|---|
| 2011/0004271 A1 | 1/2011 | Dapper et al. | |
| 2014/0253702 A1* | 9/2014 | Wexler | A61F 9/08 348/62 |
| 2015/0211858 A1* | 7/2015 | Jerauld | G02B 27/017 701/541 |
| 2017/0278308 A1 | 9/2017 | Bleiweiss et al. | |
| 2018/0131926 A1* | 5/2018 | Shanks | H04N 13/383 |

OTHER PUBLICATIONS

Dr. Dobb's | The OpenCV Library | Nov. 1, 2000, Nov. 1, 2000 URL:http://www.drdobbs.com/open-source/the-opencv-library/184404319, last accessed on: Oct. 11, 2017.

Shengcai Liao, et al., "Learning Multi-scale Block Local Binary Patterns for Face Recognition," ICB 2007, LNCS 4642, pp. 828-837, Springer-Verlag Berlin Heidelberg 2007.

Kaiming He, et al., "Delving Deep into Rectifiers: Surpassing Human-Level Performance on ImageNet Classification," Microsoft Research, arXiv:1502.01852v1 (cs.CV), Feb. 6, 2015, 11 pages.

Olga Russakovsky, et al., "ImageNet Large Scale Visual Recognition Challenge," International Journal of Computer Vision (IJCV) 115 (2015) 211-252, 43 pages.

Ross Girshick, et al., "Rich feature hierarchies for accurate object detection and semantic segmentation," Tech report (v5), arXiv:1311.2524v5 (cs.CV), Oct. 22, 2014, 21 pages.

Shaoqing Ren, et al., "Faster R-CNN: Towards Real-Time Object Detection with Region Proposal Networks," arXiv:1506.01497v3 (cs.CV), Jan. 6, 2016, 14 pages.

Joseph Redmon, et al., "You Only Look Once: Unified, Real-Time Object Detection," arXiv:1506.02640v5 (cs.CV), May 9, 2016, 10 pages.

Wei Liu, et al., "SSD: Single Shot MultiBox Detector," arXiv:1512.02325v5 (cs.CV), Dec. 29, 2016, 17 pages.

Kai Kang, et al., "T-CNN: Tubelets with Convolutional Neural Networks for Object Detection from Videos," IEEE, arXiv:1604.02532v4 (cs.CV), Aug. 3, 2017, 11 pages.

Kai Kang, et al., "Object Detection from Video Tubelets with Convolutional Neural Networks," arXiv:1604.04053v1 (cs.CV), Apr. 14, 2016, 9 pages.

Tsung-Yi Lin, et al., "Microsoft COCO: Common Objects in Context," arXiv:1405.0312v3 (cs.CV) Feb. 21, 2015, 15 pages.

Alan W. Black, et al., "The Festival Speech Synthesis System," The Centre for Speech Technology Research, Informatics Forum, Human Communication Research Centre, University of Edinburgh, Scotland, UK (1997) Available at: http://www.cstr.ed.ac.uk/projects/festival, last accessed: Oct. 11, 2017.

Willie Walker, et al., "Sphinx-4: A Flexible Open Source Framework for Speech Recognition," Sun Microsystems, SMLI TR-2004-139, Nov. 2004, 15 pages.

Zdenek Kalal, et al., "Tracking-Learning-Detection," IEEE Transactions on Pattern Analysis and Machine Intelligence, vol. 34, No. 7, Jul. 2012, pp. 1409-1422.

Yangqing Jia, et al., "Caffe: Convolutional Architecture for Fast Feature Embedding," arXiv: 1408.5093v1 (cs.CV), Jun. 20, 2014, 4 pages.

* cited by examiner

OBJECT RECOGNITION AND PRESENTATION FOR THE VISUALLY IMPAIRED

CROSS-REFERENCE TO RELATED APPLICATIONS

This application is a continuation-in-part of co-pending U.S. application Ser. No. 16/363,012, filed Mar. 25, 2019, and claims the benefit of U.S. Provisional Application No. 62/695,959, filed on Jul. 10, 2018; the entire contents of both applications are hereby incorporated herein by reference in their entirety.

TECHNICAL FIELD

Example embodiments generally relate to visual imagery analysis and, more particularly, relate to apparatuses, systems, and methods for analyzing visual imagery data for presentation in usable formats for the visually impaired.

BACKGROUND

The ability for humans to visually sense features within the environment is a fundamental capability that enables effortless interaction with everyday objects. Too frequently, individuals find themselves with limited or severely impaired vision due to degenerative disorders, trauma, or other diseases. Such impairment can make mobility and interaction with objects an arduous task. While some solutions are available to assist the visually impaired in narrowly tailored ways, these solutions are often limited in applicability due to the fragmented nature of the solutions.

BRIEF SUMMARY OF SOME EXAMPLES

Various example embodiments of apparatuses, systems, and methods for object recognition, location, and presentation for the visually impaired are provided herein. In this regard, for example, an apparatus configured to perform object recognition is provided. The apparatus may comprise a camera configured to capture a plurality of images and to transmit the plurality of images to processing circuitry, and an assistance feedback device having a field of view that is positionable by a user. The assistance feedback device may be in communication with the processing circuitry, and the assistance feedback device field of view may correspond to a current camera position. The processing circuitry configured to receive the plurality of images from the camera. The processing circuitry may be further configured to repeatedly determine characteristic features within the plurality of images and compare the characteristic features within the plurality of images to an object identification dataset to determine object matches for identified objects within the plurality of images. Additionally, the processing circuitry may be configured to determine a name for identified objects from the object identification dataset, output, using the assistance feedback device, a position indicator for identified objects, and output the name of identified objects within the assistance feedback device field of view.

According to some example embodiments, a system for performing object recognition is provided. The system may comprise an assistance feedback device that comprises a visual prosthesis. The assistance feedback device may have a field of view that is positionable via movement of a user. The system may also comprise remote apparatus. The remote apparatus may comprise a camera configured to capture a plurality of images and processing circuitry. The processing circuitry may be configured to receive the plurality of images from the camera. Further, the processing circuitry may be configured to repeatedly determine characteristic features within the plurality of images and compare the characteristic features within the plurality of images to an object identification dataset to determine object matches for identified objects within the plurality of images. Additionally, the processing circuitry may be configured to determine a name for identified objects from the object identification dataset, output, using the assistance feedback device, a position indicator for identified objects to the user, and output the name of identified objects within the assistance feedback device field of view.

According to some example embodiments, an example method for performing object recognition is provided. The example method may comprise receiving, at processing circuitry, a plurality of images from a camera, repeatedly determining characteristic features within the plurality of images, comparing the characteristic features within the plurality of images to an object identification dataset to determine object matches for identified objects within the plurality of images, determining a name for identified objects from the object identification dataset, outputting, via the assistance feedback device, a position indicator of for identified objects, and outputting the name of identified objects within the assistance feedback device field of view.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

Figure 9:
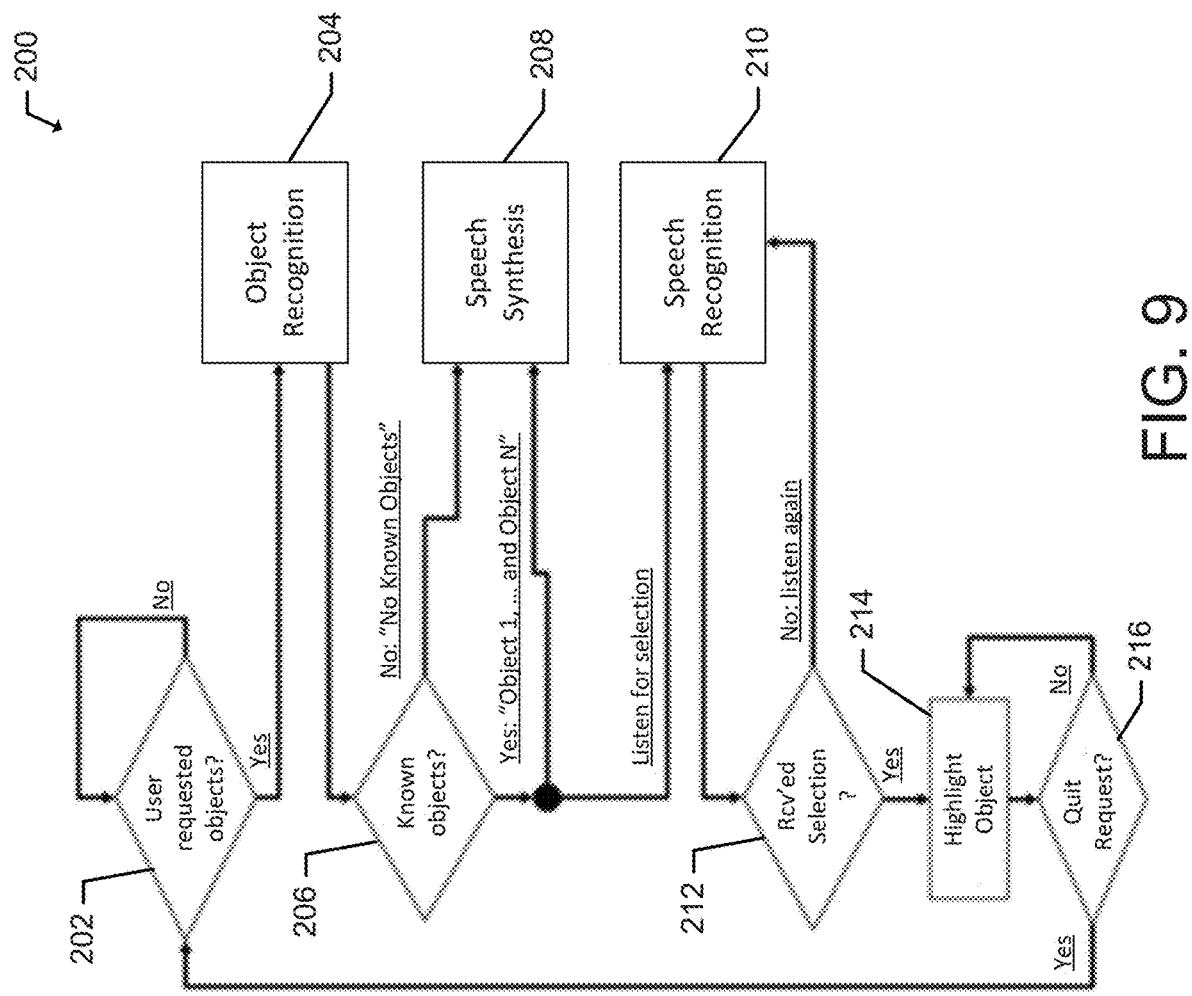
Figure 10:
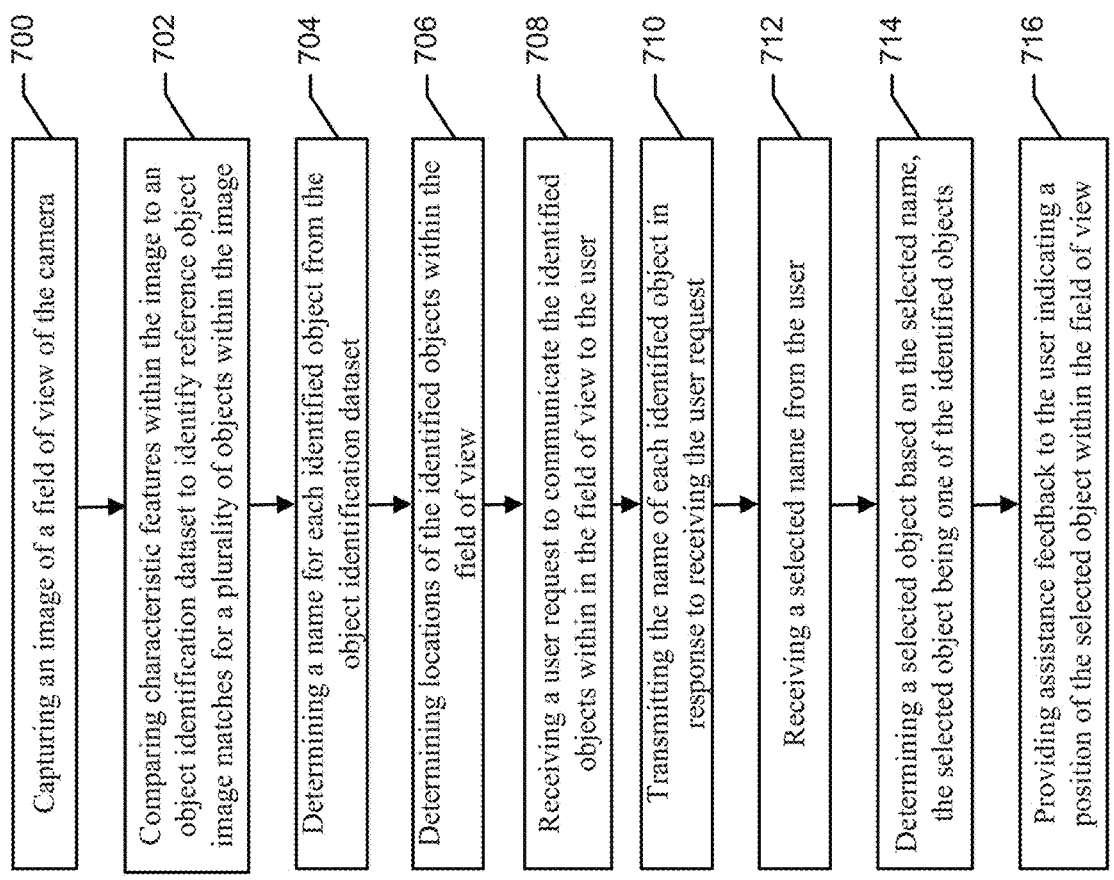
Figure 11:
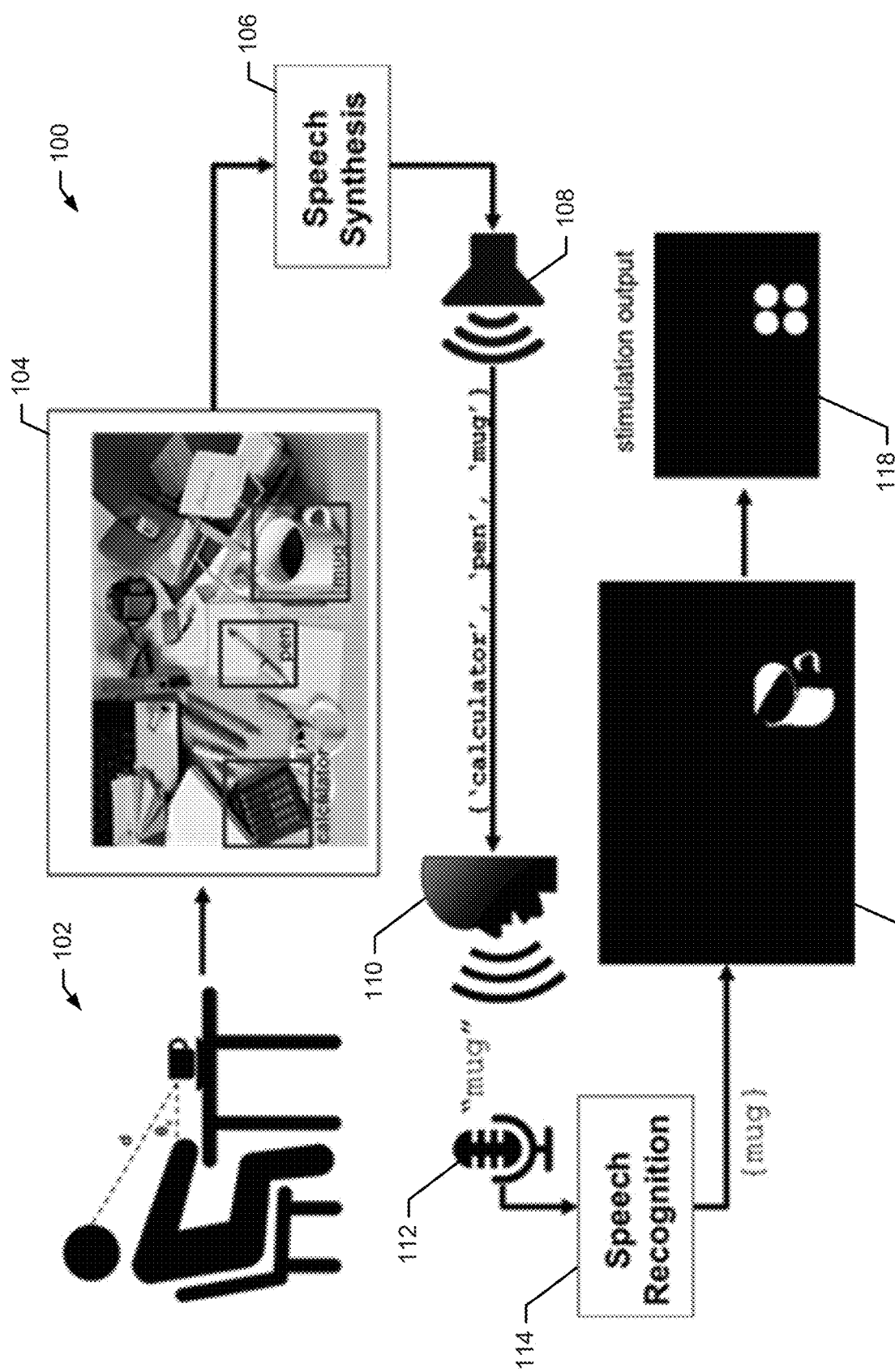
Figure 12:
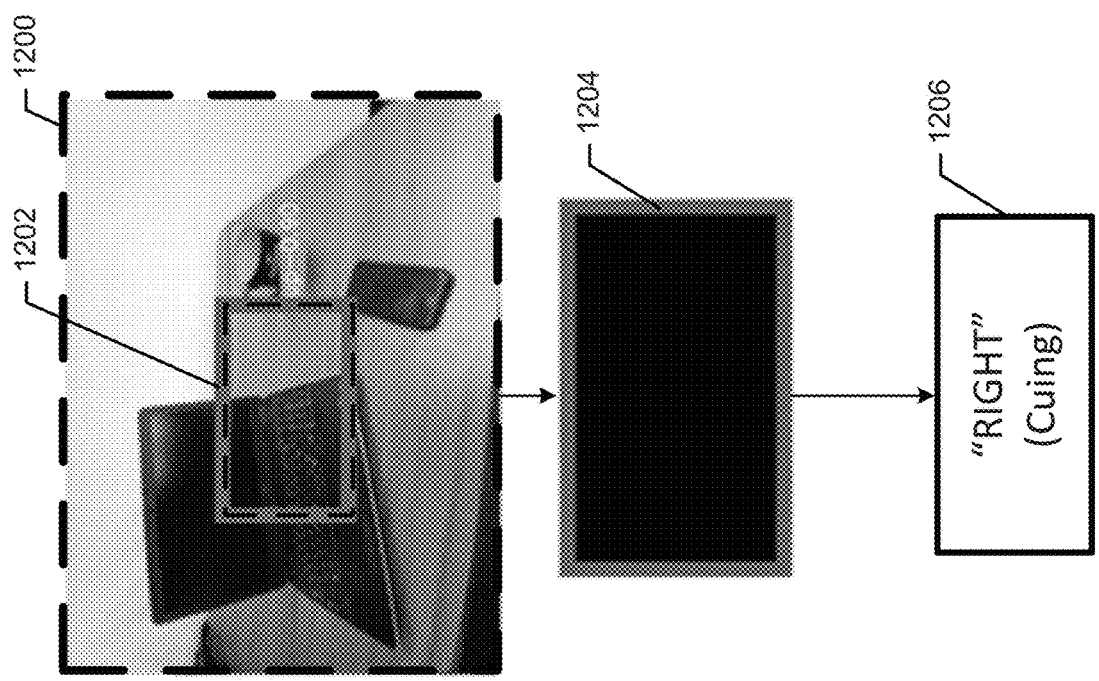
Figure 13:
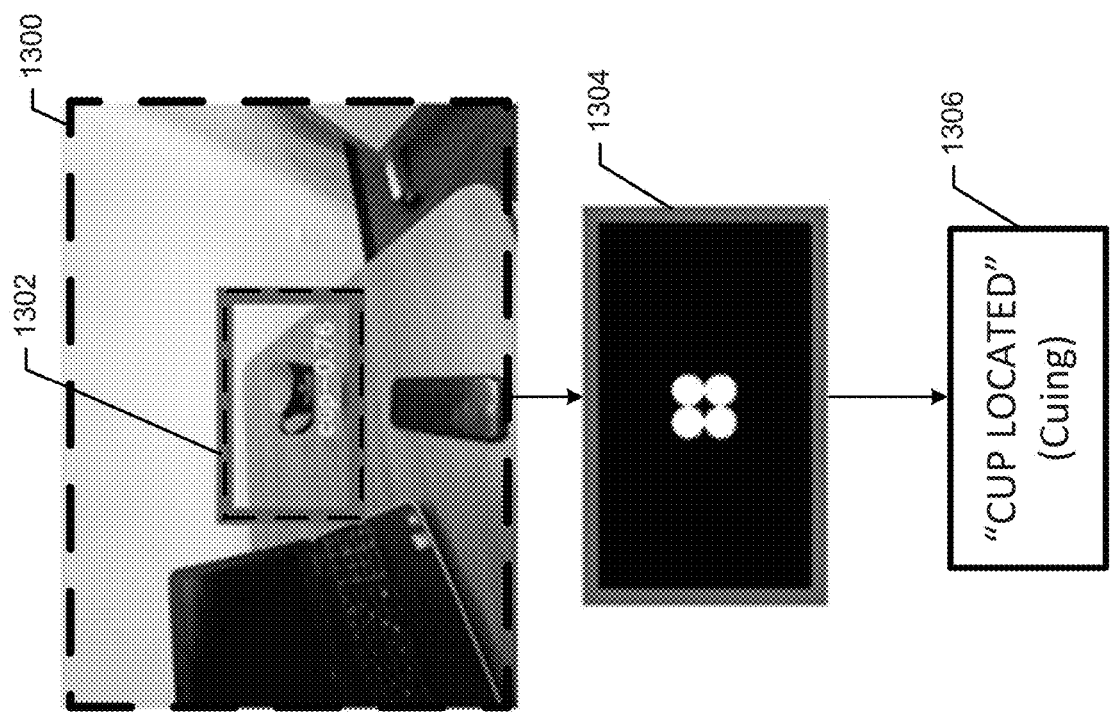

FIG. 9 provides an example flowchart for object recognition and presentation for a search mode according to an example embodiment;

FIG. 10 shows an example flowchart for object recognition and presentation for a search mode according to an example embodiment;

FIG. 11 illustrates an example interaction between a user and an object recognition and presentation system including aspects of a search mode according to an example embodiment;

FIG. 12 shows an example of cuing with the selected object outside of the field of view of the assistance feedback device according to an example embodiment; and FIG. 13 shows an example of cuing with the selected object now centered within the field of view of the assistance feedback device according to an example embodiment.

DETAILED DESCRIPTION

Some example embodiments will now be described more fully hereinafter with reference to the accompanying drawings, in which some, but not all example embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numerals refer to like elements throughout.

As used herein the term "or" is used as the logical or where any one or more of the operands being true results in the statement being true. As used herein, the phrase "based on" as used in, for example, "A is based on B" indicates that B is a factor that determines A, but B is not necessarily the only factor that determines A.

U.S. application Ser. No. 15/206,453, filed Jul. 11, 2016, now U.S. Pat. No. 10,013,599, issued Jul. 3, 2018, is hereby incorporated by reference in its entirety.

The advancement of medical device technology continues to provide new innovations that can assist individuals in overcoming medical limitations, such as the loss of sight. With respect to visual impairment, great strides have been made in the area of visual prostheses and other vision enhancement devices, more generally referred to as assistance feedback devices herein, to provide sight or enhance an individual's ability to see. Such devices can operate in a manner that essentially communicates directly with biological systems, such as the optic nerve, to provide visual information to the individual's brain for analysis and decision making. As such, by leveraging the abilities made available by such vision enhancement devices, new forms of assistance can be provided to the visually impaired to assist in tasks such as object recognition, locating, and presentation and facilitate interaction with objects in their surroundings.

According to various example embodiments, devices and methods are provided herein to leverage image capture and assistance feedback systems to assist with identification and interactions with the objects. In this regard, images captured by a camera (e.g., imaging sensor) that is, for example, head-mounted or a component of or affixed to glasses or spectacles, can be analyzed to identify discrete objects within the images. The identities or names of the objects may be provided to the individual, for example, via audio feedback or haptic feedback (e.g., a refreshable braille display) when such a system is in an "explore mode." After identification and receipt of the names of the objects near the user via the explore mode, the user may wish to select one of the identified objects. Upon selection of an object by a user, for example, via a voice to text interface or haptic input, the system may enter a "search mode." In the search mode, for example, a modified version of the captured images may be provided to the user indicating a position of the selected object within the field of view of an assistance feedback device. In some instances, the selected object may not be in a field of view of the assistance feedback device which is presented to the user. However, the selected object may, in some instances, be in the field of view of the camera and therefore be included within the capture images. In such a scenario, according to some example embodiments, the system may cue the user to indicate a direction to turn (e.g., move the user's head and, for example, the head-mounted system) to bring the selected object into the field of view of the assistance feedback device. Such cuing may be communicated to the user in a number of ways, including, for example, audible cuing, visual cuing, or haptic cuing. In response to the cuing provided by the system, the user may move (e.g., turn the user's head) to change the field of view of the assistance feedback device to bring the selected object into the field of view of the assistance feedback device. Regardless of how the selected object comes into the field of view of the assistance feedback device, the assistance feedback device may be controlled to filter or highlight the selected object to assist the user with locating and interacting with (e.g., picking up) the selected object.

In this regard, the assistance feedback device, according to some example embodiments, may be any device, whether implanted or external to the body, which operates to provide visual information to optical sensory biologic systems of the body (e.g., the eye, retina, optic nerve, visual cortex of the brain, lateral geniculate nuclei (LGN), or the like). Such assistance feedback devices may have an associated field of view and visual information may be provided within a spatial context relative to the within the field of view. Examples of assistance feedback devices may include visual prostheses such as, for example, a retinal prosthesis, a neural prosthesis, a cortical implant, a heads up display (HUD), a head mounted display (HMD) or optical head mounted display (OHMD) comprising, for example, image rendering goggles or glasses, or the like.

Figure 1:
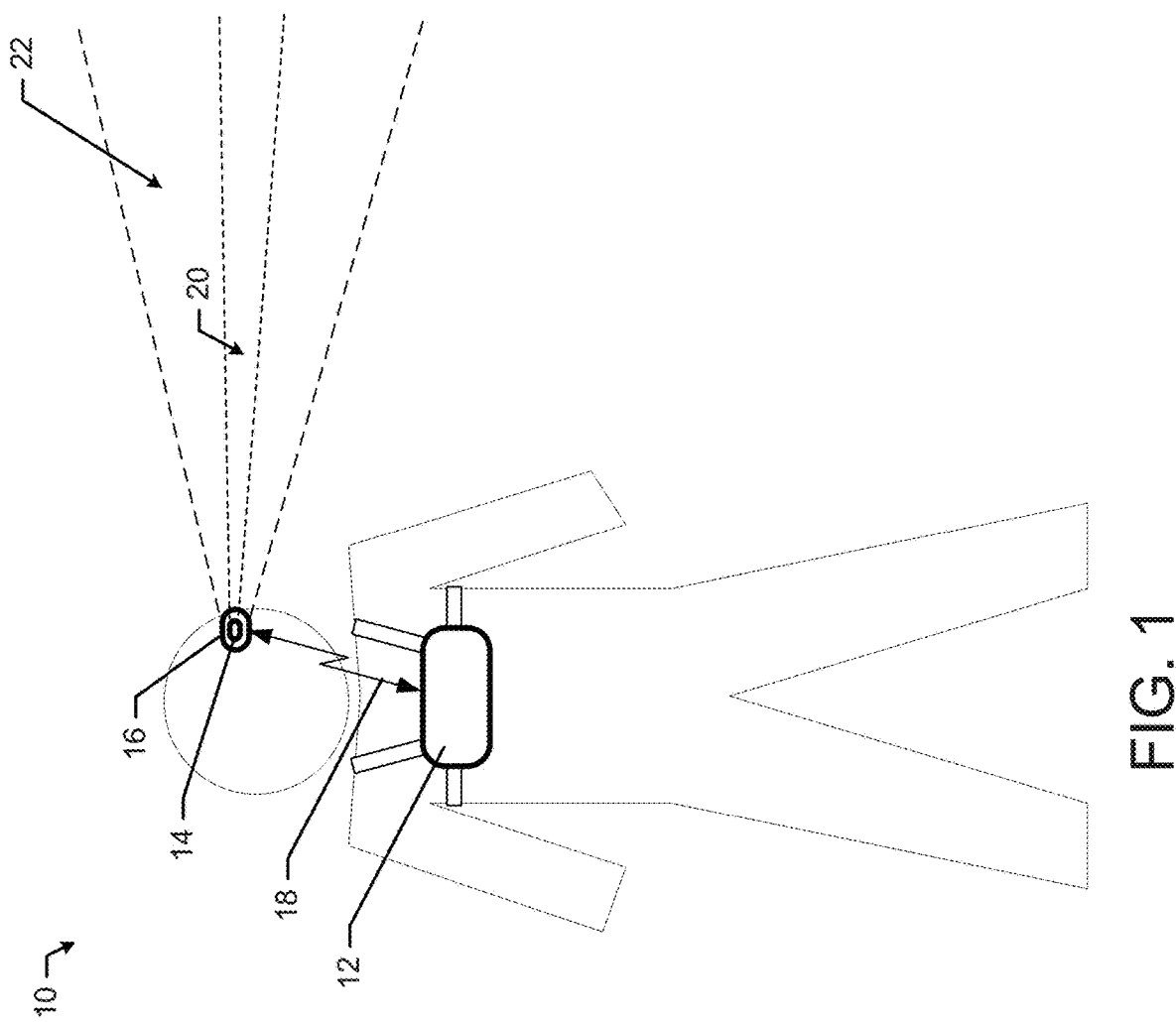
FIG. 1 shows an example system for object recognition, location, and presentation mounted or otherwise coupled to a user according to some example embodiments.

To provide general context, FIG. 1 illustrates an example system 10 configured to perform object recognition, location, and presentation to, for example, a visually impaired person according to some example embodiments. In this regard, the system 10 may include a processing apparatus 12, an assistance feedback device 14, and a camera 16. The processing apparatus 12 may be configured to perform local processing to support the object recognition, location, and presentation functionalities described herein. In this regard, the processing apparatus 12 as shown in FIG. 1 may be supported by a backpack, but any type of mobile enclosure may be used to house the processing apparatus 12. For example, according to some example embodiments, the processing apparatus 12 may be part of, for example, a device implanted in the body, co-located with the camera 16, embodied as a smartphone or other multi-use processing device, or the like. As shown in FIG. 1, the processing apparatus 12 may have a communication link 18 (e.g., wired or wireless) with the camera 16 and the assistance feedback device 14.

The camera 16, which is shown here as being head mounted, may be configured to operate as an input device to the system 10 for capturing images of the user's surroundings for analysis by the processing apparatus 12. The camera 16 may be positionable by the user via, for example, movement of the user's head in a desired direction. The camera 16 may have a field of view 22 (also referred to as a capture field of view) that defines a volume from which light is received to generate an image capture. The camera 16 may be configured to capture repeated images, possibly in the form of video capture, for use in analyzing the user's surroundings. The camera 16 may also be configured to provide the captured images to the processing apparatus 12 via the communications link 18.

The assistance feedback device 14, as described above, may provide the user with feedback information about the user's surroundings. The assistance feedback device 14 may be disposed as a device implanted in the body or may be an external display device that may be co-located with the camera 16 on, for example, glasses or goggles. The assistance feedback device 14 may also be in communication with the processing apparatus 12 (e.g., wired or wireless), possibly via communications link 18 to receive feedback information from the processing apparatus 12 for presentation to the user. The feedback information may be presented as a field of view 20 (also referred to as the presentation field of view) of the assistance feedback device 14 to the user, and, according to some example embodiments, the presentation field of view 20 of the assistance feedback device 14 may be smaller than the capture field of view 22 of the camera 16. However, because the camera 16 and the assistance feedback device 14 may be positionable by the user in a coordinated fashion (e.g., because both are positionable via movement of the head) the capture field of view 22 of the camera 16 may be spatially associated (i.e., the field of view 22 for the camera 16 moves with the field of view 20 for the assistance feedback device 14 such that there is no relative movement). In this regard, for example, the presentation field of view 20 of the assistance feedback device 14 may be located within the capture field of view 22 of the camera 16. According to some example embodiments, the presentation field of view 20 of the assistance feedback device 14 may be located centrally within the capture field of view 22 of the camera 16. However, due to, for example, variations in the location of the assistance feedback device 14 when implanted, the presentation field of view 20 of the assistance feedback device 14 may not be located centrally within the capture field of view 22 of the camera 16, and a calibration process may be performed to associate the presentation field of view 20 with the capture field of view 22. Accordingly, movement of the user's head can operate to provide the user with information about the user's surroundings in a spatial context to facilitate the user's interaction with objects identified by the system 10 in the user's surroundings, as further described herein.

Figure 2:
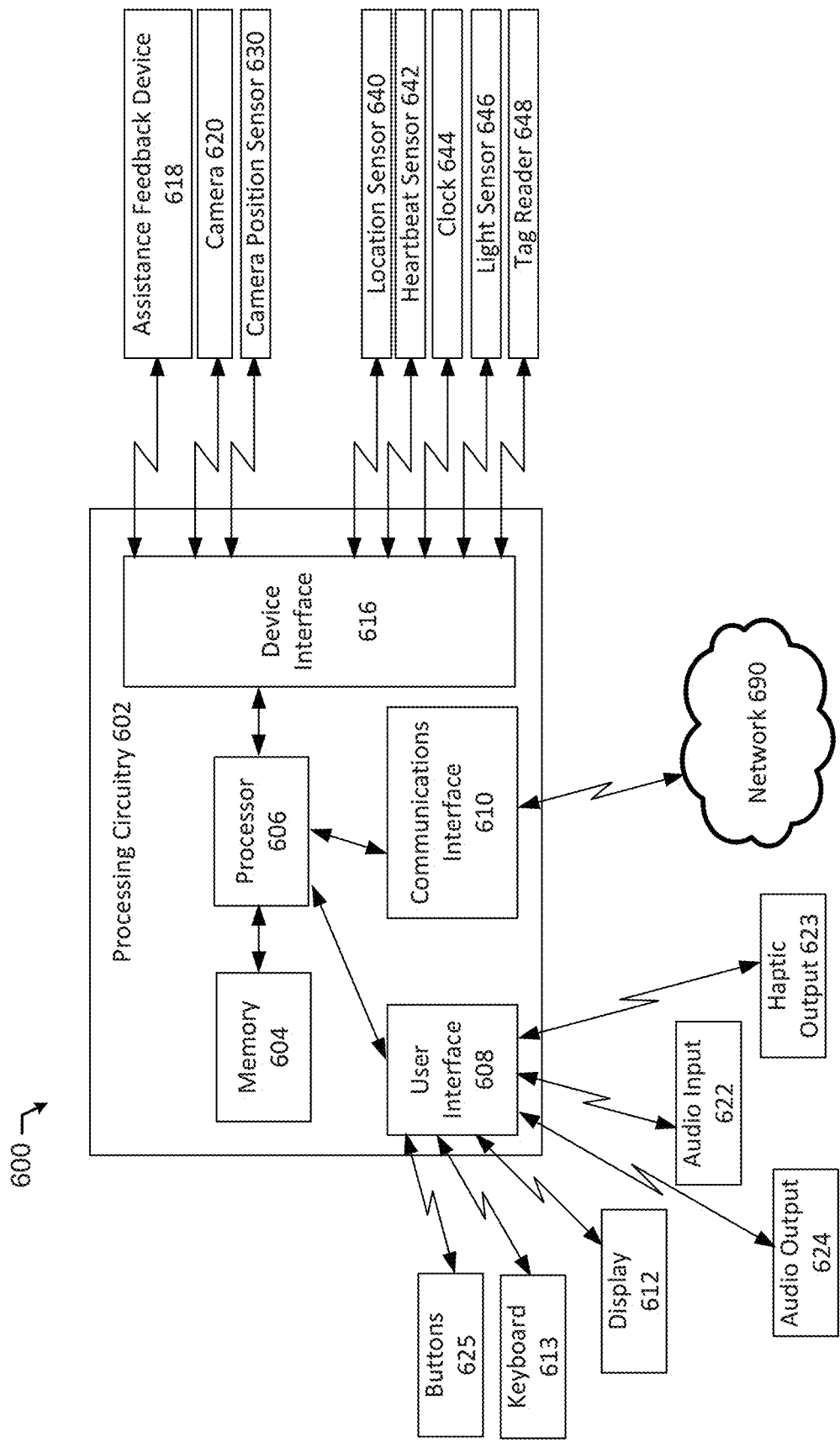
FIG. 2 shows an example apparatus for object recognition, location, and presentation according to an example embodiment.

With reference to FIG. 2, an example apparatus 600 and certain components thereof will now be introduced and described that can be used to implement various example embodiments described herein. For example, the apparatus 600 may be a component of or embody the system 10 of FIG. 1 and may operate in a similar manner. In this regard, FIG. 2 provides a block diagram including some select components of an example apparatus 600 configured to perform various types of object recognition, location, and presentation according to some example embodiments.

In general, the apparatus 600 may include processing circuitry 602, which may be embodied and operate in a similar manner to the processing apparatus 12 of system 10. The processing circuitry 602 may include a processor 606 and a memory 604. As further described below, the processing circuitry 602 may be configurable to perform various operations according to some example embodiments. Further, the apparatus 600 and the processing circuitry 602 may include a user interface 608 which interfaces with various types of input and output devices to receive input from and provide output to the user. The processing circuitry 602 may also include a communications interface 610, which may be configured to communicate with any type of wired or wireless device. Additionally, the processing circuitry 602 may also include a device interface 616 configured to interface with various sensors or other types of devices including, for example, an assistance feedback device 618 (which may be same or similar to the assistance feedback device 14) and a camera 620 (which may be the same or similar to the camera 14). As such, the device interface 616 may be configured to interface with visual assistance components (e.g., assistance feedback device 618, camera 620, and camera position sensor 630) and user context components (e.g., location sensor 640, heartbeat sensor 642, clock 644, light sensor 646, tag reader 648, or the like).

In this regard, the apparatus 600 may include processing capabilities that may be performed by processing circuitry 602. In this regard, processing circuitry 602 may be in operative communication with or embody the communications interface 610, the user interface 608, and the device interface 616. The processing circuitry 602 may interact with or embody the memory 604 and the processor 606. According to some example embodiments, the processing circuitry 602 may be configurable (e.g., as hardware or via execution of software instructions) to perform various operations described herein. In some embodiments, the processing circuitry 602 may be embodied as a chip, chip set, or collection of chip sets. In other words, the processing circuitry 602 may comprise one or more physical packages (e.g., chips) including materials, components, or wires on a structural assembly (e.g., a baseboard). The processing circuitry 602 may be configured to receive inputs (e.g., via the user interface 608, communications interface 610, device interface 616, memory 604, or the like), perform actions based on the inputs, and generate outputs (e.g., for provision to peripheral components). In an example embodiment, the processing circuitry 602 may include one or more instances of the processor 606, associated circuitry, and the memory 604. Further, the processing circuitry 602 may be embodied as a circuit chip (e.g., an integrated circuit chip, such as a field programmable gate array (FPGA)) configured (e.g., with hardware, software, or a combination of hardware and software) to perform operations described herein.

In an example embodiment, the memory 604 may include one or more non-transitory memory devices such as, for example, volatile or non-volatile memory that may be either fixed or removable. The memory 604 may be configured to store information, data, applications, instructions or the like for enabling, for example, object recognition, location, and presentation and to carry out various functions in accordance with exemplary embodiments. For example, the memory 604 could be configured to buffer input data for processing by the processing circuitry 602. Additionally or alternatively, the memory 604 could be configured to store instructions for execution by the processing circuitry 602. Among the contents of the memory 604, applications may be stored for execution by the processing circuitry 602 in order to carry out the functionality associated with each respective application.

As mentioned above, the processing circuitry 602 may be embodied in a number of different ways. For example, the processing circuitry 602 may be embodied as various processing means such as one or more processors 606 that may be in the form of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processing circuitry 602 may be configured to execute instructions stored in the memory 604 or otherwise accessible to the processing circuitry 602. As such, whether configured by hardware or by a combination of hardware and software, the processing circuitry 602 may represent an entity (e.g., physically embodied in circuitry—in the form of processing circuitry 602) capable of performing operations according to example embodiments while configured accordingly. Thus, for example, when the processing circuitry 602 is embodied as an ASIC, FPGA, or the like, the processing circuitry 602 may be specifically configured hardware for conducting the operations described herein. Alternatively, as another example, when the processing circuitry 602 is embodied as an executor of software instructions, the instructions may specifically configure the processing circuitry 602 to perform the operations described herein.

The communication interface 610 may include one or more interface mechanisms for enabling communication with other devices external to apparatus 600, via, for example, a network 690, such as a local area network. In some cases, the communication interface 610 may be any means such as a device or circuitry embodied in either hardware, or a combination of hardware and software that is configured to receive or transmit data from/to devices in communication with the processing circuitry 602. The communications interface 610 may be a wired or wireless interface and may support various communications protocols.

The user interface 608 may be controlled by the processing circuitry 602 to interact with a user. In this regard, via the user interface 608, the processing circuitry 602 may be configured to output to a user via an output device such as, for example, driving a display 612 to provide a visual output and receive input from a user via an input device such as, for example, audio input 622, which may be, for example, a microphone. The user interface 608 may also produce outputs, for example, via audio output 624, which may be for example, a speaker, bone-conduction headphones, or the like. According to some example embodiments, the user interface may also operably couple to other user input devices such as, for example, a keyboard 613, buttons 625, a mouse, a touch screen, or the like. Further, the user interface 608 may also be in communication with a haptic output 623. In this regard, the haptic output 623 may be a separate device that physically couples to the user (e.g., to the user's hand or elsewhere on the user's body) or is included or integrated into another device, such as, for example the assistance feedback device 618. According to some example embodiments, the haptic output 623 may be embodied as a refreshable braille display that can provide information to the user via touch.

The device interface 616 may be configured to interface with various devices and sensors including special purpose devices that may be closely controlled (possibly via firmware) by the processing circuitry 602. While shown as separate interfaces in FIG. 2, according to some example embodiments, the device and components connected to the processing circuitry 602 via the user interface 608 or the communications interface 610, may alternatively be coupled or connected to the processing circuitry 602 via a single interface or a group of interfaces, such as, for example, the device interface 616. In this regard, the device interface 616 may, for example, include a data bus (e.g., universal serial bus (USB)) that devices may be connected to for interaction with the processing circuitry 602. Via the device interface 616, the processing circuitry 602 may send control messages or output information to a device via the device interface 616, and the processing circuitry 602 may receive circumstantial information from devices that may, at least in part, be used to modify the configuration or operation of processing circuitry 602 based on the circumstantial or user context information.

According to some example embodiments, the apparatus 600 may include or be operably coupled to the assistance feedback device 618, for example, via the device interface 616 (or the user interface 608). The assistance feedback device 618 may be the same or similar to the assistance feedback device 14 of the system 10. As described above, the assistance feedback device 618, according to some example embodiments, may be any device, whether implanted or external to the body that operates to provide visual information as a visual output to optical sensory biologic systems of the body (e.g., the eye, retina, optic nerve, visual cortex of the brain, lateral geniculate nuclei (LGN), or the like). Such assistance feedback devices may have an associated field of view for presenting visual information in a spatial context to the user. Examples of assistance feedback devices 618 may comprise visual prostheses such as, for example, a retinal prosthesis, a neural prosthesis, a cortical implant, an HUD, an HMD, or an OHMD comprising, for example, image rendering goggles or glasses, or the like. According to some example embodiments, the assistance feedback device 618 may be configured to implement image augmentation features that integrate feedback information into a visual scene provided, for example, by a transparent display, or through stimulation of a prosthesis, or the like.

According to some example embodiments, the assistance feedback device 618 may be configured to, directly or indirectly, send communications to the processing circuitry 602 or receive communications from the processing circuitry 602. Communications with the assistance feedback device 618 may be performed via, for example, coupled coils. In this regard, for example, a first coil implanted in the user's body and connected to an implanted portion of the assistance feedback device 618 may be configured to form a communication link with a second coil disposed external to the body and connected to the processing circuitry 602 either via a wired or wireless coupling. According to some example embodiments, the assistance feedback device 618 may comprise a display (e.g., retinal or other biologic structure stimulator, HUD, HMD, OHMD, or the like) that can provide visual information in the form of feedback to a user for the purpose of communicating information about the user's surroundings to permit the user to interact with her surroundings as provided herein. Further, according to some example embodiments, the assistance feedback device 618, as mentioned above, may include a controllable inertial device or the like that can provide haptic feedback to a user (e.g., may include haptic output 623). Further still, according to some example embodiments, the assistance feedback device 618 may include audio output capabilities (e.g., may include audio output 624) that can provide feedback to the user. Additionally, in one embodiment, the assistance feedback device 618 may provide a combination of audio, visual, and haptic feedback or outputs to the user.

The device interface 616 may also operably couple to a camera 620, which may be the same or similar to the camera 16 described above. The camera 620 may be configured to capture an image of a field of view for the camera and transmit that image, for example, to the processing circuitry 602. The camera 620 may be configured to capture two-dimensional (2D) images or three-dimensional (3D) images in a digital format and communicate the images to the processing circuitry 602 for analysis as provided herein. According to some example embodiments, the camera 620 may be a time of flight camera configured to capture four dimensional images with one of the dimensions being depth (e.g., Red Green Blue video with depth (RGB-D)). Further, the camera 620 may be configured to capture repeated images, possibly in a video mode, for provision to the processing circuitry 602 for analysis.

The apparatus 600 may also include a camera position sensor 630. The camera position sensor 630 may be configured to track the pointing position or the field of view of the camera 620. In this regard, the camera position sensor 630 may include location positioning circuitry that uses global positioning system (GPS), received signal strength, time-of-arrival signal analysis, or the like to determine a position of the camera 620. The camera position sensor 630 may also determine the orientation of the camera 620. To do so, the camera position sensor 630 may include gyros, accelerometers, or the like to capture information regarding the pitch, roll, and yaw of the camera 620. Further, the camera position sensor 620 may also include a compass or other magnetic device configured to determine a pointing direction of the camera 620. The camera position sensor 630 may therefore track the pointing position or the field of view of the camera 620 to generate camera position information that indicates the position, orientation, and pointing position of the camera 620 at a particular time. The camera position information may be provided in a manner that permits the camera position information to be associated with images captured by the camera 620, for example, via time stamp correlation. As such, through image analysis and the camera position information, real-world positions of, for example, objects identified in the images captured by the camera 620 can be determined and stored for later use.

The apparatus 600 may also include a variety of other devices, such as, sensors that can capture contextual information about the user for use in object recognizing, locating, and presenting and provide the captured information to the processing circuitry 602, possibly via the device interface 616. In this regard, for example, the apparatus 600 may include a location sensor 640. The location sensor 640 may be configured to determine a location of the apparatus 600 and provide location information describing the location of the apparatus 600 to the processing circuitry 602 as contextual information about the user, also referred to as user context information. The location sensor 640 may include location positioning circuitry that uses GPS, received signal strength, time-of-arrival signal analysis, or the like to determine a position of the apparatus 600. In this regard, in example embodiments where the camera 620 is located with the user, the camera position sensor 630 may be used to generate the location information about the user.

Further, according to some example embodiments, the apparatus 600 may include health sensors for generating additional health or status context information about the user. For example, the apparatus 600 may include a heartbeat sensor 642 to generate information regarding the user's heartbeat. Such heartbeat information may be used to determine a status of the user (i.e., working out, sleeping, etc.). The apparatus 600 may also include a clock 644 to generate time information regarding the date and the time of day. Such time information may be coupled with a stored schedule of the user (e.g., meeting schedule, activity schedule, etc.) to provide further information regarding the context of the user. Additionally, the apparatus 600 may include a light sensor 646 to provide light information indicating whether the user is in a lit environment or a dark environment as additional user context information.

The apparatus 600 may also include a tag reader 648 that is configured to read nearby tags, such as, RFID tags. In this regard, the tag reader 648 may also be able to provide user context information based on being proximate or near certain tags that may be present in an environment. For example, a tag may be placed within each room of house and the tag reader 648 may be able to read the tag in the room to determine which room of the house the apparatus 600 is currently located within. Further, a tag be placed in a vehicle to allow the tag reader 648 to determine when the apparatus 600 is in a vehicle. Accordingly, tags may be used to assist with determining location information as well as other user context information. For example, a tag may be placed on a moving object, such as another individual or a pet to determine when the user is near the person or pet to provide additional user context information.

Figure 3:
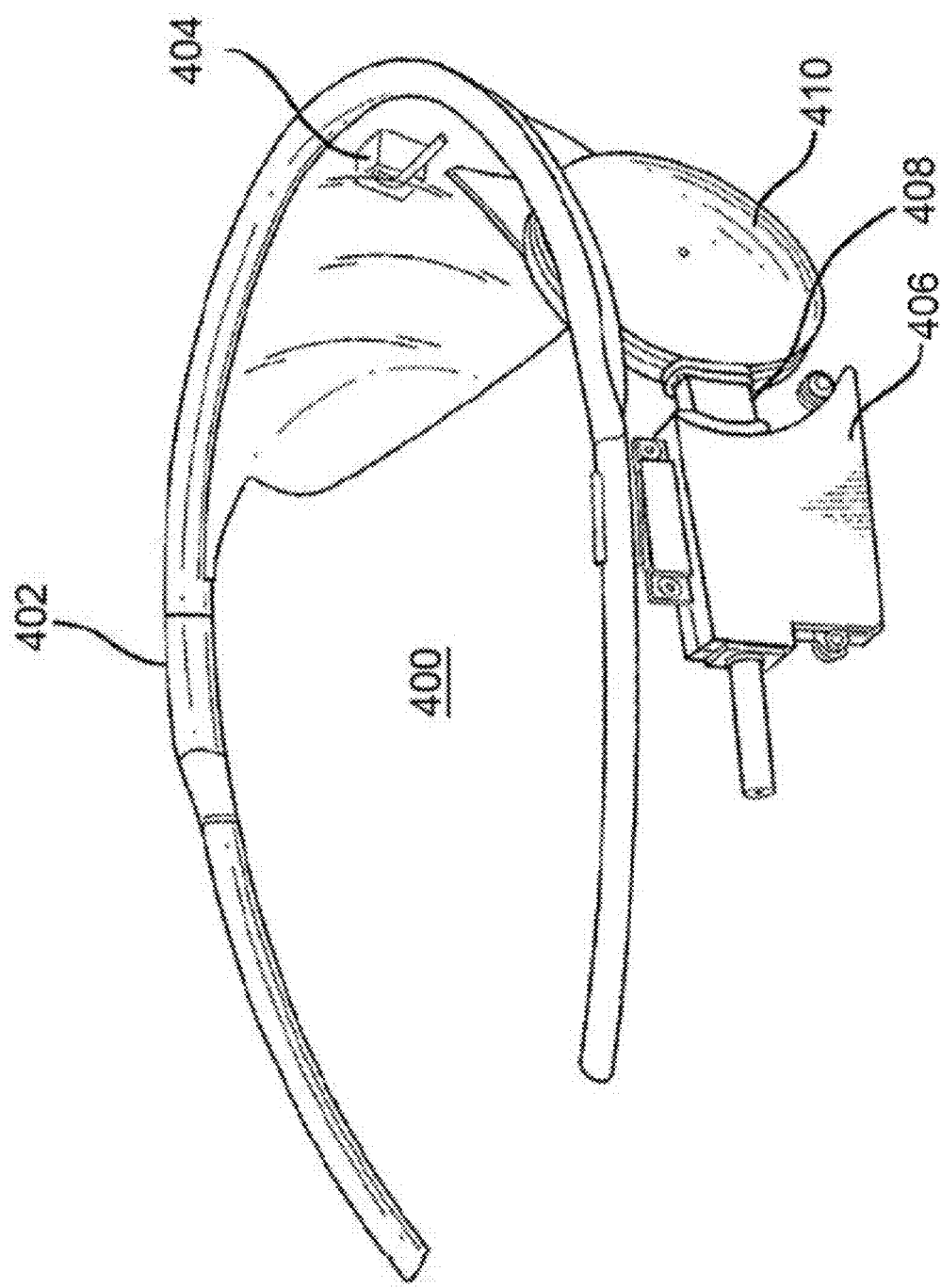
FIG. 3 shows a glasses component with a camera according to an example embodiment.
Figure 4:
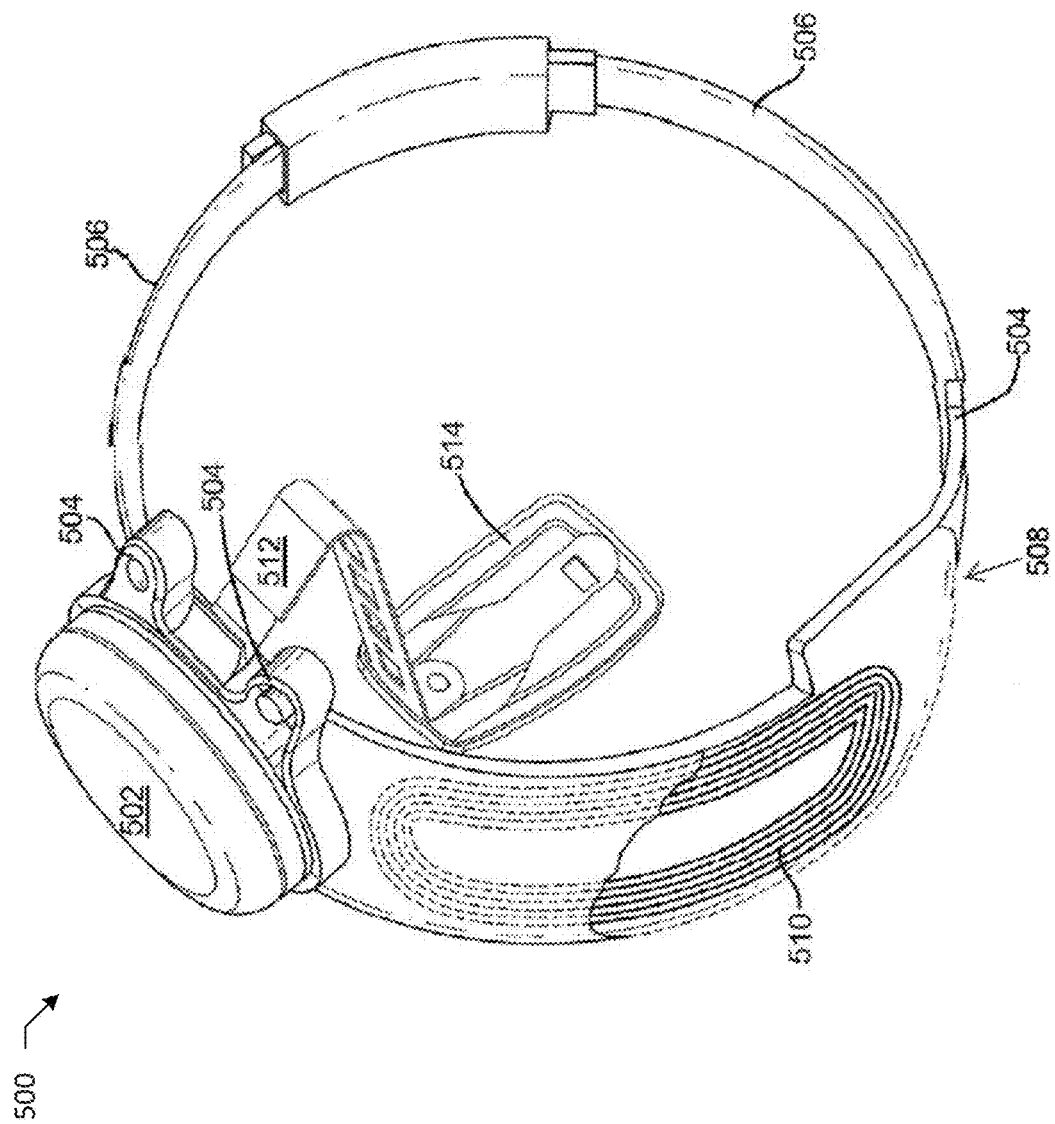
FIG. 4 shows a assistance feedback component in the form of a retinal prosthesis according to an example embodiment.

Now referring to FIGS. 3 and 4, according to some example embodiments, an apparatus may be embodied by glasses 400 and retinal prosthesis 500 that may be configured to operate the same or similar to the apparatus 600. The electronics housing 406 of the glasses 400 may house, for example, the processing circuitry 602 and the other components of the apparatus 600, with the exception of the assistance feedback device 618 which may be embodied as the retinal prosthesis 500. In this regard, FIGS. 3 and 4 show components of an example system or apparatus that may be configured to perform object recognition and presentation in accordance with various example methods and techniques described herein. FIG. 3 shows glasses 400 that are worn external to the body and FIG. 4 shows a retinal prosthesis 500 that may be implanted into, the eye of a user.

Referring to FIG. 3, the glasses 400 may include, for example, a frame 402 holding a camera 404 (e.g., camera 620), an external coil 410, an external coil support 408, and an electronics housing 406 operably coupled to the external coil 410 and the camera 404. The electronics housing 406 may also enclose processing and communications circuitry, as described above with respect to apparatus 600. Glasses 400 may also have an audio output (e.g., audio output 624, which may include one or more speakers, bone-conduction headphones, or the like) and an audio input (e.g., audio input 622, which may include one or more microphones, or the like). According to some example embodiments, the glasses 400 may include a screen for providing a visual output. In this configuration, the camera 404 may be configured to capture images including still images or live video and generate a digital representation of the field of view of the camera 404. The digital representation may be sent to processing circuitry (e.g., processing circuitry 602, possibly housed in the electronics housing 406) for analysis and to take appropriate action as described herein, such as, generate electrical stimulation patterns that may be communicated to the retinal prosthesis 500 for provision to the user.

With regard to the retinal prosthesis 500 of FIG. 4, the electrical stimulation data (that provides a stimulation image as a visual output) may be sent via the external coil 410 and, for example, radio-frequency (RF) telemetry to an internal coil 510 of the retinal prosthesis 500. The internal coil 510 may receive the communicated information and transmit the information to processing circuitry of the electronics package 502, which may be a microprocessor, an ASIC, an FPGA, or the like. The processor of the electronics package 502 may in turn deliver stimulation to the retina of a user or subject via an electrode array 514. Array 514, according to some example embodiments, may be a 60-channel electrode array. The electrical stimulation patterns or data may be passed via electrodes of the array 514 that cause retinal cells to be stimulated thereby providing a visual output. As described herein, the technique of stimulating the retinal cells to permit a user to visualize an image or information may be one example technique of rendering the image or information for interpretation by the user.

The retinal prosthesis 500, which is an example of an assistance feedback device 618, may be implanted for interaction with the retina of a visually impaired individual. A flexible circuit associated with the implanted portion of the retinal prosthesis 500 may include the array 514 which is mounted by a retinal tack (not shown) or similar means to the epiretinal surface. The array 514 may be electrically coupled by a flexible circuit cable 512, which pierces the sclera, to electronics package 502, which may be external to the sclera. The electronics package 502 may, include a processor, and be electrically coupled to an internal coil 510. The processor of the electronic package 502 may work together with the processing circuitry of the electronics housing 406 to implement various aspects of the example embodiments described herein. The internal coil 510 may receive power and data from an external coil 410, which is external to the body as described above. The electronics package 502 and internal coil 510 may be held together by a molded body 508. The molded body 508 may include suture tabs 504 for securing the retinal prosthesis 500 in the body. The molded body 508 may narrow to form a strap 506 which surrounds the sclera.

Figure 5:
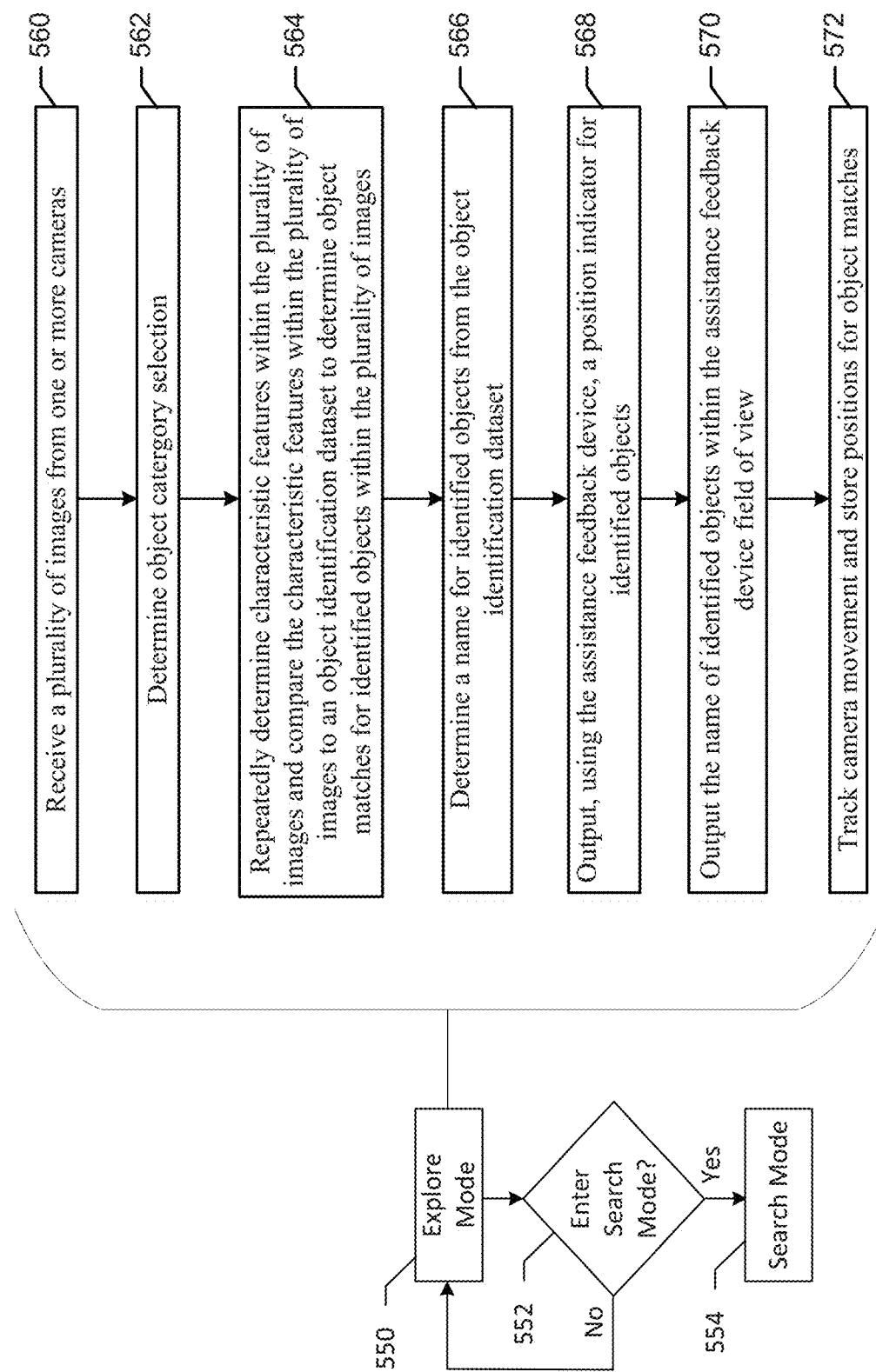
FIG. 5 shows a flowchart of an explore mode of operation according to some example embodiments.

With the description of FIGS. 1-4 providing some example embodiments of the systems and apparatus that may be utilized as described herein, a description of various example methods and scenarios will now be provided that may be implemented by the systems and apparatuses of FIGS. 1-4. In this regard, FIG. 5 provides a flowchart of an example method for implementing an example explore mode 550 and an example search mode 554, with a more detailed description of the example explore mode 550. Generally, according to some example embodiments, in the explore mode 550, a user may, after initiating the explore mode, move the camera 620 to scan the user's surroundings and the apparatus 600 may be configured to, for example, verbally output names of the objects and present position indications of the objects that are identified in the user's surroundings via the assistance feedback device 618. The names and position indications of the identified objects may be automatically communicated in real-time or near real-time as the user scans the surroundings.

In this regard, according to some example embodiments, a user may initiate explore mode 550, via, for example, a device connected to the user interface 608 by verbal command as received by the audio input 622, key-typed command as received by keyboard 613, or the like. Upon initiating the explore mode 550, the processing circuitry 602 may begin to, or continue to, receive, at 560, images (e.g., a plurality of images provided in a serial manner) from the camera 620 that have been captured by the camera 620. According to some example embodiments, an object category selection may be determined at 562, as further described in detail below. Additionally, according to some example embodiments, the processing circuitry 602 may be configured to, at 564, repeatedly determine characteristic features within the plurality of images through various techniques for feature extraction and compare the characteristic features within the plurality of images to an object identification dataset to determine object matches for identified objects within the plurality of images.

In this regard, according to some example embodiments, the processing circuitry 602 may be configured to repeatedly compare characteristic features within at least some of the images to the object identification dataset to identify object matches for the plurality of objects within the images. The object identification dataset may comprise a database of information about objects and visual characteristics of the objects for use in performing object identification. The object identification dataset may include information regarding any number and type of objects. For example, the object identification dataset may include information regarding the visual characteristic features of object from a baseball to a giraffe to an individual's face. Further, according to some example embodiments, face information may be included in the object identification dataset to facilitate performance of facial recognition. Techniques for facial recognition may be found in, for example, U.S. Pat. No. 10,013,599, issued on Jul. 3, 2018, the entire contents of which are hereby incorporated by reference.

To identify object matches, the processing circuitry 602 may leverage a convolutional neural network (CNN) to compare the characteristic features to the object identification dataset and determine matches resulting in detection of the object. Additionally, as further described below and with respect to FIG. 6, rather than repeatedly leveraging the CNN to determine object matches, according to some example embodiments, a tracking technique may be employed that increases the efficiency of keeping track of a position of an identified object within newly captured images by implementing a filter (e.g., a Kalman filter) and then performing the analysis of the characteristic features with reduced frequency. Further, a confidence threshold may be set and only objects that are identified that meet or exceed the confidence threshold may be considered identified objects.

The comparison of image features to an object identification dataset (e.g., for object recognition), using for example a CNN, may be used to evaluate one or more images. According to some example embodiments, an object detection technique or algorithm may make an error in detection for example by detecting an object that is not actually present (i.e., a false positive) or may fail to recognize an object that is present (i.e., a false negative). Variation in detection output associated with such errors may occur, for example, with even subtle changes between input images. As a result, when running object detection on frames from a video sequence, the detection output may not be completely consistent from one frame to the next, due to intermittent errors appearing in some frames but not others. This issue may be exacerbated when using still captures of video from a moving camera due to, for example, variation in the image quality and sharpness of the still captures arising from motion blur. As such, undesirable spurious or intermittent detections may flicker in and out from one frame to the next, which may cause confusion and diminish utility for the user. To address this problem, according to some example embodiments, object tracking may be used between frames of a video sequence in order to, for example, reject intermittent detection errors. For example, spurious detections may be rejected by excluding detections that appear in a less than a threshold number of frames (e.g., only appear in one or a few frames). Intermittent true detections may be consistently displayed to the user in every frame by, for example, using object tracking to carry over detections from prior frames. According to some example embodiments, such an object tracking technique may also be used when object recognition is run at a slower interval relative to a video image capture speed, which may happen when the computational load for the processing circuitry is, for example, too great for object recognition to keep up or which may be done as an energy conservation strategy. Thus, images may be analyzed for object recognition, for example, at relatively slow intervals (e.g., two images per second) or at fast intervals (e.g., video intervals such as thirty images per second) using various techniques. As such, according to some example embodiments, other faster tracking-based techniques may be implemented, as described below, that do not, for example, rely upon a CNN for all object recognition image analysis.

However, object recognition robustness may be increased by evaluating an increased number of images that, for example, include the same objects such as subsequent image captures in a sequence. As such, implementing object recognition across multiple image captures (e.g., where the image captures are of a threshold quality or sharpness) may be beneficial to obtain highly reliable object recognition results. Therefore, according to some example embodiments, object recognition may be performed by comparing the object identification data set to many image captures that, for example, include the same objects, such as multiple sequentially captured images, to generate robust and stable object recognition.

Figure 6:
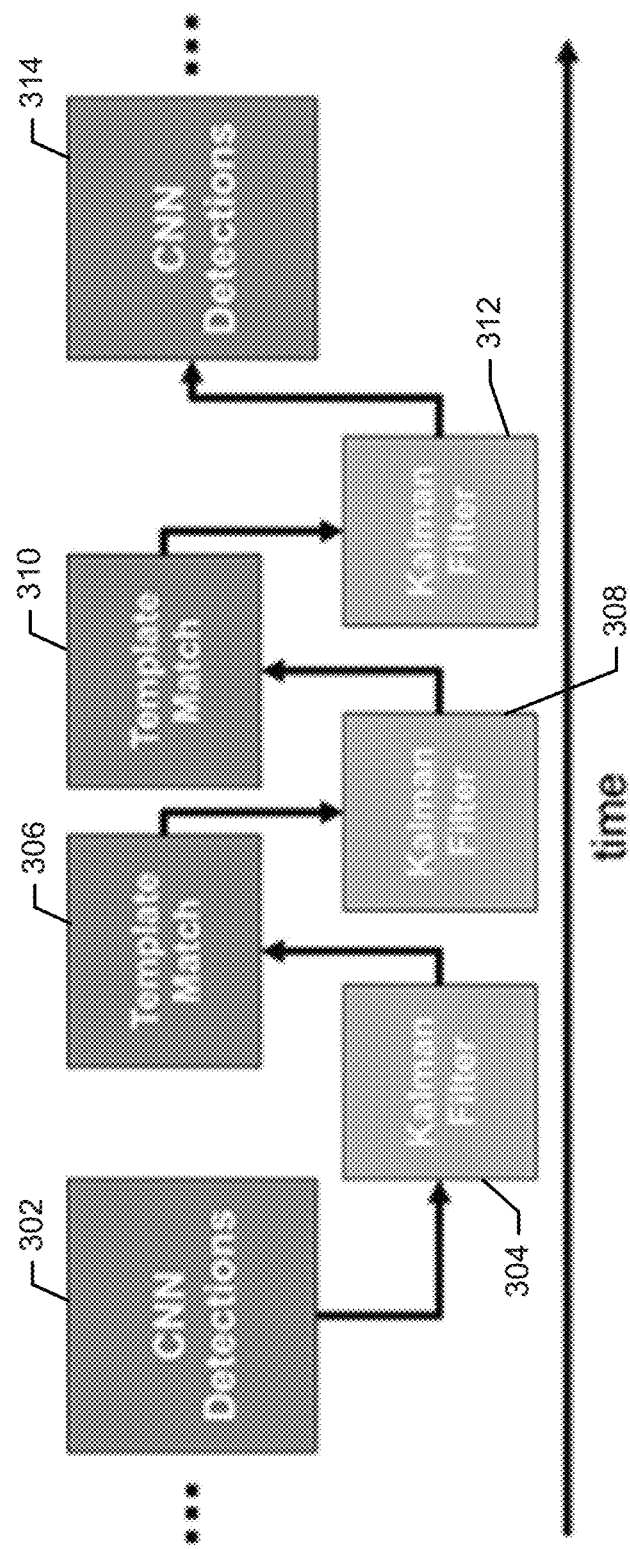
FIG. 6 illustrates an example object tracking approach according to an example embodiment.

Further, according to some example embodiments, the images used for object recognition may be filtered and movement may be accounted for using template matching techniques between object recognition events as provided here and further described with respect to FIG. 6. For example, object identification may be performed on every n-th image (e.g., every third video image) after being subjected to filtering and image matching. A Kalman filter is one example of a temporal filter that focuses on stability and may be applied in this context. Other example filters that may be alternatively used in this regard include moving average filters and Gaussian temporal filters. The goal of the image filtering is to improve tracking of the objects over time, which is particularly relevant during times when object recognition fails to find a match. Thus, the application of the filter provides temporal stability of the objects detected.

Based on the object matches and the associated identified objects, the processing circuitry 602 may also be configured to determine, at 566, a name for the identified objects from the object identification dataset. In this regard, in addition to the characteristic features for various objects, the object identification dataset may include names of objects (e.g., "cup," "pen," "phone," or the like). Accordingly, the object identification dataset may be queried to determine the names provided for the identified objects.

Further, the processing circuitry 602 may be configured to, at 568, output, using the assistance feedback device 618, a position indicator for identified objects. In this regard, position indicators may be provided for the identified objects that are within the field of view of the assistance feedback device 618. The position indicators may be provided at a position within the presented field of view of the assistance feedback device 618 that corresponds to a real-world position of an identified object. According to some example embodiments, the resolution of the assistance feedback device 618 may determine a degree of detail of the identified object provided by the position indictor. In this regard, the resolution of example assistance feedback devices 618 may be very low (e.g., 10 by 6 pixels) and therefore a dot or other mark may be provided as a position indicator for a given object. However, in some example embodiments, an assistance feedback device 618 may have higher resolution and thus a more detailed rendering of the identified object may be provided. In some example embodiments where image augmentation is implemented, the assistance feedback device 618 may draw a circle or box around the identified objects on a transparent display to provide the position indicator.

Further, according to some example embodiments, the processing circuitry 602 may be configured to, at 570, output the name of identified objects within the assistance feedback device 618 field of view. In this regard, the names of the identified objects may be output, for example, audibly by speaking the name of the identified objects using speech synthesis. Additionally or alternatively, the names of the identified objects may be output to a display (e.g., display 612 or a display for the assistance feedback device 618) to provide a visual indication of the names of the identified objects. Further, the names of the identified objects may be provided to a haptic output 623, such as, for example, a refreshable braille display to provide the names of the identified objects to the user.

The process of identifying objects and outputting position indicators and names of the objects may be repeated for as long as the apparatus 600 remains in explore mode 550. As such, according to some example embodiments, the operations as described with respect to operations 560, 564, 566, 568, 570, and 572 may be repeated to identify new objects and output new position indicators and new names. The operations may repeat, for example, until the apparatus 600 exits explore mode 550. In this regard, the processing circuitry 602 may be configured to make a determination, at 552, whether, for example, a trigger to enter search mode 554 has occurred. Such a trigger may be a user request to locate an object received, for example, by the audio input 622, or a defined change in user context based on context information as described above.

Additionally, as mentioned above, at 562, the processing circuitry 602 may determine an object category selection. The object category selection may be used to control the universe of objects that may be identified or communicated to a user while implementing, for example, explore mode 550. According to some example embodiments, the object category selection may be received, for example, from a user input device, such as, for example, audio input 622, keyboard 613, or the like. In this regard, a user may input a category of objects that may be used to limit the position indicators and names that are output during implementation of the explore mode 550. The object identification dataset may include object categories associated with the objects or object names. The object category selection may be used to query the object identification dataset to generate a subset for objects that satisfy the object category selection. Alternatively, the object category selection may be applied after the objects are identified, and then the position indicators and names for the identified objects that are within the category selection may be output. Further, the object identification dataset may be reduced or expanded based on the object category selection to determine the object matches for the identified objects. As such, according to some example embodiments, the processing circuitry 602 may be configured to determine object matches for identified objects, where the identified objects satisfy the object category selection (i.e., are within the category associated with the object category selection).

For example, a user may provide input as "dinnerware" for the object category selection. As a result, the processing circuitry 602 may receive the object category selection of "dinnerware" and apply the object category selection such that position indicators and names for identified objects that are, for example, forks, spoons, knives, plates, cups, and the like are provided, while no position indicators or names are provided for non-dinnerware, such as pens, pencils, phones, and the like because these objects are not within the object category selection.

According to some example embodiments, rather than receiving the object category selection directly from a user request, the object category selection may be determined, wholly or partially, based on the user context information. Such user context information may be based on information generated by a user context device or sensor, such as, for example, location sensor 640, heartbeat sensor 642 or other health sensors, clock 644, light sensor 646, tag reader 648, or the like. In this regard, information from one or more of these sources may be received and possibly aggregated to generate an object category selection to be applied as provided above. As such, the processing circuitry 602 may be configured to receive the user context information from one or more user context sensors and determine an object category selection based on user context information. According to some example embodiments, user context information may be combined with category selection provided by the user (e.g., audibly) to determine the object category selection. Again, the processing circuitry 602 may be configured to determine the identified objects based on satisfaction of the object category selection.

In this regard, for example, based on location information provided by the location sensor 640 various determinations of an object category selection may be made. If the location information indicates that the user is located in her home, then an object category selection that encompasses objects that are likely to be found in the home may be added as candidate objects (i.e., the objects satisfying the object category selection) for analysis. Such objects may include, for example, a chair, cabinet, sofa, light switch, television, dog, table, fork, pencil, or the like, while other non-candidate objects (i.e., the objects not satisfying the object category selection) may be removed from a group of possible candidate object options, such as, for example, train, steering wheel, picnic table, bird, mailbox, or the like. However, as the user moves into other surroundings, the group or subset of possible candidate objects may be reduced or expanded. In this regard, if, for example via the location sensor 640 or the tag reader 648, the user context information indicates that the user has moved into the garage, then, for example, a fork may be removed from the possible candidate objects, while a cabinet, light switch, and pencil may remain, and a screwdriver, garage door opener button, and vehicle may be added. As such, based on the user context information repeated changes to the group of possible candidate objects can be updated based on the definition of the object category selection.

Similarly, based on user context information from, for example, the location sensor 640 and possibly, the light sensor 646, the processing circuitry 602 may be configured to determine that the user and the apparatus 600 have moved into a building. Accordingly, the processing circuitry 602 may be configured to adjust the object category selection to remove objects that would be associated with an outdoor setting. Further, upon receipt of additional user context information from, for example, the location sensor 640 and possibly, the light sensor 646, a determination may be made that the user and the apparatus 600 have now moved to an outdoor setting. As such, objects that would be associated with an outdoor setting may be returned and therefore would satisfy the updated object category selection based on the new user context information.

In combination with user context information in the form of, for example, location information, other non-sensor information may be considered in the definition of the object category selection, such as, for example, map information. In this regard, based on the user's position, as indicated by the location information, surrounding landmarks as indicated in map data may be identified and included in the object category selection.

Some further examples may include, if the location sensor 640 indicates that the user is at the gym with a low heart rate as indicated by the heartbeat sensor 642, then the objects satisfying the object category selection may include restroom signs, but if the heart rate is high and being maintained, then the user may be actively working out, possibly on a treadmill, and the object category selection may be redefined to include a water bottle, a towel, and aspects of the treadmill's user interface.

As mentioned above, the time of day may also be considered as provided by the clock 644. Additionally, an electronic schedule may also be considered as non-sensor data in association with the location information. As such, the apparatus 600 may be able to determine that the user is at meeting in the office and the object category selection may be defined accordingly. For example, the participants in the meeting may be determined from the invitees and face recognition may be performed. As such, the schedule is another example of the use of non-sensor data for contribution to the determination of an object category selection.

Further, according to some example embodiments, the determination of an object category selection may be based on objects that have been recently identified. For example, if a keyboard is identified, the object category selection may be defined such that a mouse may satisfy the object category selection. In this regard, complementary objects may be defined that are often nearby when one of the objects is present.

Accordingly, the determination of the object category selection may be complex and determined based on sensor inputs, non-sensor contextual data (e.g., user schedule, map data, or the like), verbal and non-verbal inputs from the user, the identification of other objects, and the like. As such, the determination of the object category selection may be multidimensional based on these various inputs that may be considered to develop the object category selection, and, as such, a dynamic range of possible object category selections may be defined.

Additionally, the processing circuitry 602 may be configured to, at 572, to track the camera movement, for example, via the camera position sensor 630, and determine and store positions of identified objects. In this regard, the positions of the identified objects may be stored in, for example, memory 604. Further, over time, the positions of identified objects may be stored in, for example, a historical database and refreshed as new identifications of objects are performed. As mentioned above, with respect to the operation of the camera position sensor 630, the camera position information may be used with the captured images to identify and determine a position for objects. The determined position may then be stored for later use with respect to cuing the user to move in a particular direction to bring a desired object that is currently outside the field of view of the camera 620 or the assistance feedback device 618, into the field of view of the assistance feedback device 618 as further described below.

Additionally, tracking may be performed within the field of view of the camera 620. To do so, according to some example embodiments, the processing circuitry 602 may be configured to apply a filter, as mentioned above, to captured images over time to estimate positions of the identified objects based on a prior location determination of the identified objects between iterations of comparing the characteristic features to the object identification dataset. The filter may be, for example, a Kalman filter applied to the more than one captured image. Further, the processing circuitry 602 may also be configured to generate matching templates. The matching templates, which may, according to some example embodiments, include distilled, shape-based representations of features of an object identified in a captured image and may be applied to subsequent captured images. By applying the matching templates, the system may perform one or more template match iterations to provide a streamlined technique for identifying an object in other, possibly subsequent, image captures. Such filtering and application of the matching templates may be performed either between object recognition iterations (e.g., using the CNN), or in parallel with (e.g., simultaneously with) object recognition iterations (e.g., using the CNN), which may include, for example, comparing the characteristic features to the object identification dataset to captured images over time to track movement of the objects. According to some example embodiments, such filtering and application of matching templates may be applied on images where an object recognition is determined for a particular captured image, or in instances where no object recognition is determined for the particular captured image.

In this regard, with reference to FIG. 6, a process of operations for object tracking and video image filtering is shown with respect to time. Further, to provide an improved user experience, according to some example embodiments, a sequence of images may be analyzed in view of the above, particularly since a user's field of view may be dynamically changing due to, for example, head movement, or because of instability in the positions output by the object recognition algorithm in sequential frames of an image sequence with or without changing the user's field of view. As such, an object tracking capability may be implemented that visually smooths image presentations to avoid "jumpy" object recognition locations being provided to the user and to stabilize the presentation to the user.

Although not shown in FIG. 6, it is understood that image capturing is being repeatedly performed (e.g., in a video mode) over time based on the camera 620's current field of view. In this regard, at 302, an object recognition in the form of, for example, a convolutional neural network (CNN) detection may be performed to identify objects in a captured image. From this object recognition, a matching template may be defined that indicates the relative positions of objects or features within an image. The matching template may be used to track objects both in between and simultaneous to iterations of applying the CNN to captured images or frames. The matching template may be derived from a most recent bounding box provided by the object recognition result. Once the matching template is derived, the matching template may be used to track the object even when object recognition fails to find the detected object. Subsequently, at 304, a filter (e.g., a Kalman filter) may be applied to a subsequent captured image and a template match may be performed at 306 on the subsequent image using the matching template to identify movement of the objects within the field of view. Accordingly, for each image, which may be associated with time steps, a bounding shape (e.g., with a centroid width and height) may be adjusted. With the movement identified, the bounding shapes for the identified objects may be moved within the subsequent image in a corresponding manner and the result may be used for presentation to the user (i.e., with or without having performed object recognition on the subsequent image). In this regard, the movement may be represented by an estimated track state with, for example, four elements that describe the current xy position of the object and a next xy position of the object.

The filter (e.g., Kalman filter) may again be applied to a further subsequent image at 308, and yet another template match may be performed at 310 to relocate the identified objects and present the resultant modified image (e.g., in the form of a stimulation image) to the user. At 312, a filter may again be applied to a subsequent image in preparation for another object recognition at 314.

More specifically, with respect to tracking in view of the context provided above, according to some example embodiments, a Single Shot Multibox Detector (SSD) technique may be utilized. A Single Shot Multibox Detector (SSD) is one example of a high performing object recognition algorithm based on deep learning and convolutional neural networks. In this regard, when an object has been first detected by an SSD, a track for that object may be considered "soft" and initialized for the respective object since there is not yet an actual track. If the object is detected using SSD a minimum number of times (e.g., 5), then the track may be considered "hard" and the object may be added to a list of objects that continues to be included in the scene. A Kalman filter may be used at each timestep for the images in order to predict and measure the tracked object's bounding box centroid (x, y), width, and height. As such, the four elements of the estimated track state may be [$S_x$, $S_y$, $S_w$, and $S_h$] (e.g., x,y location and width and height of the tracked object). It is noted that more than one object may be tracked at a time.

To associate SSD-based detections with the tracked objects at each iteration, three criteria may be used, namely, matched class labels, minimum intersection over union (IOU), and a maximum Euclidean distance between centroids. The minimum IOU threshold, $T_{IOU}$, and the maximum distance threshold, $T_D$, may be determined empirically as follows. As mentioned above, an estimated track state may be defined by four elements that are related to an object's bounded box in x and y coordinates. In this regard, the four elements of the estimated track state may be $S_x$, $S_y$, $S_w$, and $S_h$.

In the event that no track association is found for an SSD detection, a new track may be soft initialized. Conversely, if no matching SSD detection is found for an existing hard track, then basic template matching may be employed between the most recent SSD-detected bounding box for that track and an expanded search region centered at the current track centroid ($S_x$, $S_y$). If the maximum normalized cross coefficient metric exceeds a defined threshold, $T_{TM}$, a match is declared and the matched location provided to the tracking algorithm (e.g., Kalman filter) to update the location of the tracked object in the input frame. The stored bounding box for the given track may not be updated until a new associated SSD detection has been found. At each iteration, an age of each track may be incremented or increased for soft and hard tracks. The age of tracks may be reset if an SSD association has occurred or if a template has matched. Tracks that exceed a threshold age may be removed, thereby ensuring that any objects with false positives or objects that have exited the camera 620's field of view are no longer processed.

Based on the foregoing, according to some example embodiments, camera 620 may be a 3D camera and 3D images may be utilized in object recognition and presentation as provided herein. However, the use of 3D may also allow some example embodiments to leverage the third, depth dimension of the image to further assist the visually impaired to interact with their surroundings. In this regard, the captured image or images may be filtered by depth, and areas of the scene with predetermined depth range from the user may be considered for object recognition. In this regard, a 2D image may be formed at the predefined depth for use in object recognition and presentation as provided herein.

With respect to tracking an object, according to some example embodiments, even if an object has been identified through object recognition, the object may need to appear in a minimum number of images, either through object recognition or through template tracking, to be considered an identified object for further interaction with respect to the user. As such, objects that only appear in a sequence of images for a relatively short period of time (e.g., a defined number of images as determined by an age of the object's corresponding track) need not be considered an option for interaction with the user.

Further, depth information may be used to perform cuing. A user may move the field of view to align with a selected object based on a determined centroid of a selected object in 3D (or 2D) and cuing via, for example, a spatial sound that uses, for example, a Head-Related Transfer Function (HRTF) to cue the user to the relative location of the selected object. According to some example embodiments, such auditory information could be conveyed, for example, via open-ear, bone-conducting headphones that do not interfere with the user's normal hearing. Such auditory cuing feedback may enable use by a broader visually impaired community outside of, for example, visual prosthesis users. Other means of cuing, such as using haptics or visual cuing, for example could also be used.

Figure 7:
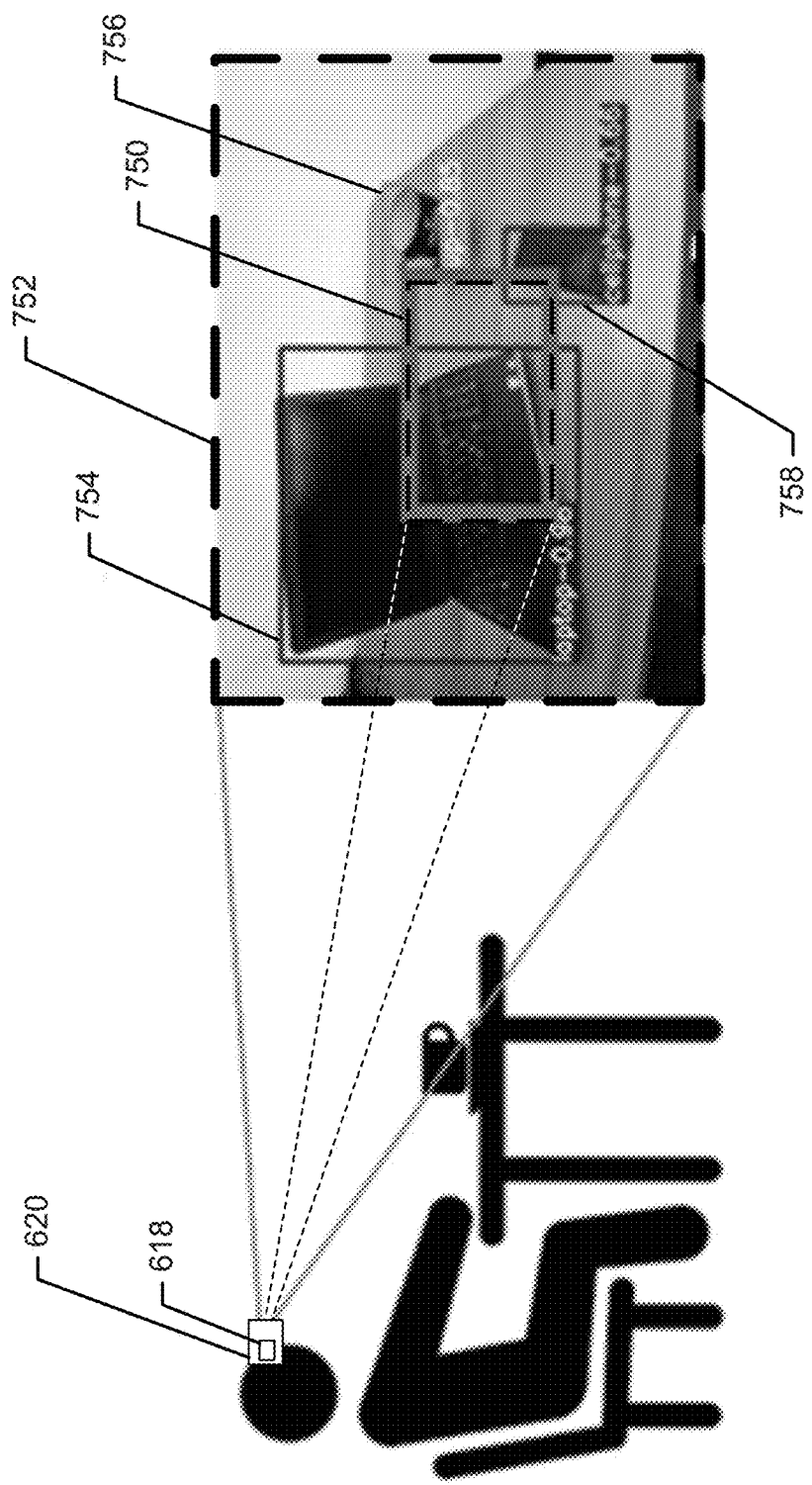
FIG. 7 shows an example environment for implementing an explore mode of operation according to some example embodiments.
Figure 8:
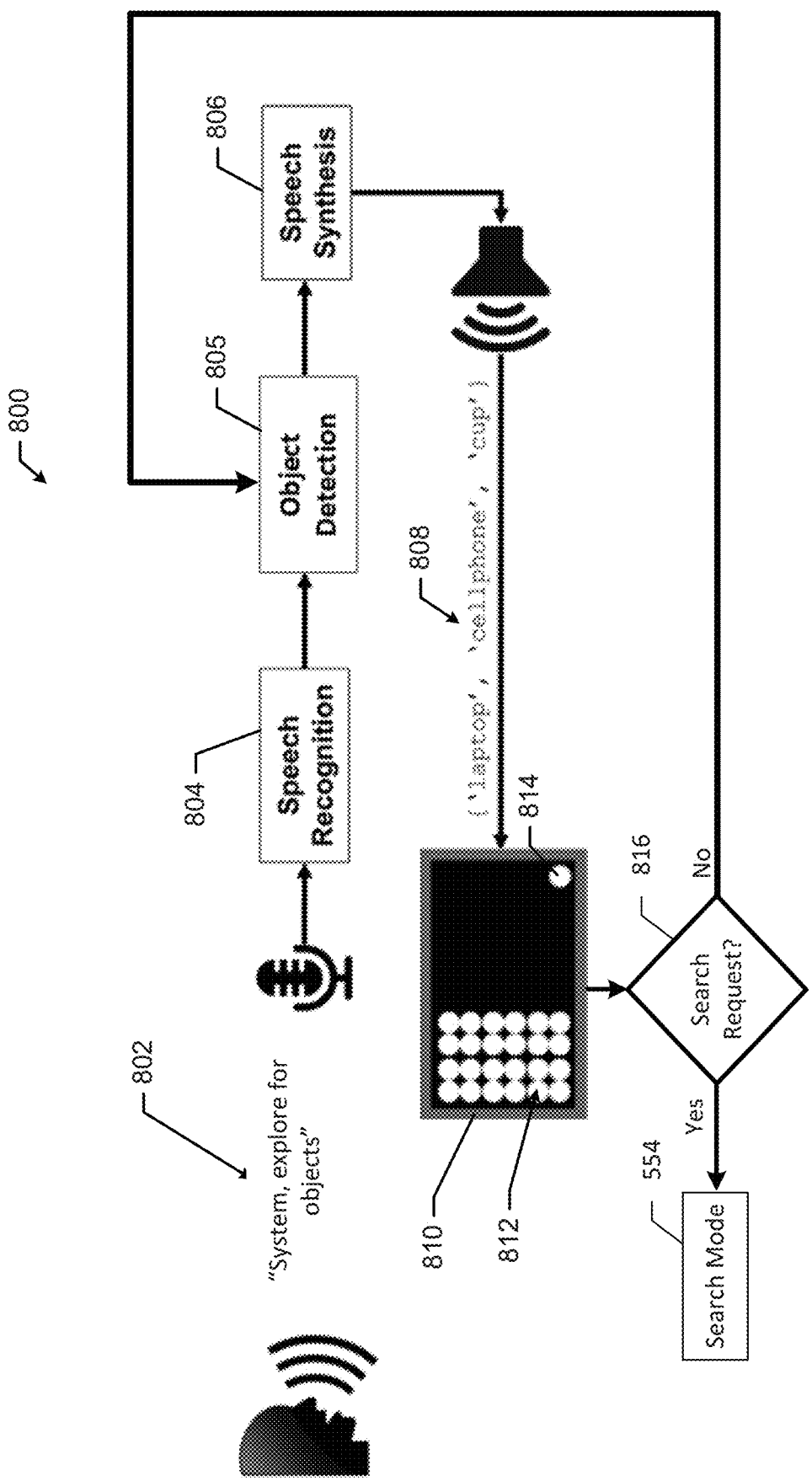
FIG. 8 shows an example scenario that is applied in the context of FIG. 7, according to some example embodiments.

Having described various aspects and embodiments of explore mode in general terms, a description of FIGS. 7 and 8 will now be provided which illustrates an example explore mode mode scenario. In this regard, with reference to FIG. 7, a user may be seated at a table with a plurality of objects (e.g., a computer, a cup, and a cellphone) on the table. As shown in FIG. 7, the camera 620, with a capture field of view 752 has captured one or more images of the tabletop. The field of view 750 of the assistance feedback device 618 is also shown.

In this regard, referring to FIG. 8, the example scenario may begin at 802 where the user initiates the explore mode. To do so, the user may provide an audible command, e.g., "System, explore for objects", which may be received by the audio input 622. The audio input 622 may provide a signal representative of the audible command to the processing circuitry 602 for speech recognition at 804 to begin explore mode. According to some example embodiments, explore mode may be performed as described above, and otherwise herein to determine the identified objects. In this case, the processing circuitry 602 may, perform object detection at 805 by determining object matches for the computer 754, for example, the cup 756, and the cellphone 758. Upon determining the names of the identified objects, the processing circuitry 602 may utilize a speech synthesis engine at 806 to enunciate the names of the identified objects at 808 via, for example the audio output 624. In this regard, the processing circuitry 602 may cause, for example, audio output 624 to enunciate information associated with the identified objects (e.g., names of the identified objects) that are either within the field of view 750 of the assistance feedback device 618 (such that the user is only informed concerning the objects that the user can currently see via assistance feedback device 618) or within the field of view 752 of the camera 620. Accordingly, the user may be informed of objects identified in the surrounding environment and which the user may not necessarily be able to see since those objects may be outside the field of view 750 of the assistance feedback device 618. As such, depending on the enunciation configuration selected by the user, the processing circuitry 602 may, for example, cause an audible output of the name "cup", despite the cup not being within the field of view 750 of the assistance feedback device 618.

Further, an example stimulation image 810 of position indicators is provided. In this regard, the stimulation image 810 may be an example of the information that may be provided via, for example, the assistance feedback device 618 in the form of, for example, a retinal prosthesis implant having a 10 by 6 pixel display. As shown, the position indications are provided as activated monochrome pixels. In this regard, referring back to the field of view 750 of the assistance feedback device 618, a portion of the computer 754 is included on the left side of the field of view 750 and a portion of the cellphone 758 is included in the lower right corner of the field of view 750. As such, in the stimulation image 810 provided by the assistance feedback device 618, the portion of the computer 754 is shown by the position indication 812, which is a cluster of activated pixels on the left side of the stimulation image 810. Further, the portion of the cellphone 758 is shown by the position indication 814 as a single pixel in the lower right corner of the stimulation image 810.

According to some example embodiments, upon providing the stimulation image 810, continued explore mode activities may be undertaken by the user by moving the camera 620's field of view 752 and the assistance feedback device 618's field of view 750. Further, according to some example embodiments, at 816, a determination may be made as to whether a request to enter search mode has been received, and if so, enter the search mode 554 as further described below. If the search mode 554 is not entered, then, for example, continued operation in explore mode may occur, with objects continuing to be detected at 805. Such detected objects may, according to some example embodiments, be automatically announced via speech synthesis at 806 or otherwise communicated to the user without further input from the user and the process may continue as described above.

Having described in relation to FIGS. 5-8, various example embodiments of systems, apparatuses, and methods configured to perform object recognition, location, and presentation in the explore mode, a description of systems, apparatuses, and method for performing search mode will now be provided, with reference back to the apparatus 600 and components thereof to implement various example embodiments of search mode. In search mode, a user may be attempting to locate a specific object. As described above, search mode may be triggered from explore mode, possibly after the desired object is named in explore mode, by providing, for example, an audible request. However, according to some example embodiments, a user may initially enter search mode with respect to, for example, a specific scene including a plurality of objects or an explicit request received from the user. In this way, according to some example embodiments, the initial operations performed in search mode may be the same or similar to those performed in explore mode, until a selection of specific objects is received.

According to some example embodiments, FIG. 9 provides a detailed flowchart of an example method 200 for object recognition and presentation in the search mode, which may be implemented by the apparatus 600 with the processing circuitry 602. Entry into search mode may occur in a number of different ways that result in receipt of a user selection of an object to be located.

In this regard, at 202, a user may make a request for an object, which may be provided in the form of a selection of an object. The request may be made in a variety of ways based on various example embodiments. For example, the user may speak a predefined phrase (e.g., "system, identify objects"), press a button, or the like that triggers a system to begin the method 200. In response, the system may be configured to communicate (e.g., announce) the objects, for example, currently in the field of view of the camera 620 or in a field of view of a feedback assistance device 618, as described herein. Upon providing a communication indicating the objects, the system may await receipt of a request from a user for a specific object, for example, by receiving an audible request (e.g., "system, find <object>" where <object> may be "cup"), or by receiving a request via other input devices that can be used to make a selection such as a keyboard, mouse, touch screen, or the like Alternatively, the search mode may be entered by receiving a request from a user for a specific object (e.g., without an initial request to identify objects), for example, by receiving an audible request (e.g., "system, find <object>" where <object> may be "cup"), or by receiving a request via other input devices that can be used to make a selection such as a keyboard, mouse, touch screen, or the like. According to some example embodiments, subsequent to receiving the request for the specific object (e.g., and before the specific object has been located), the system may still receive a request to identify the objects in the current field of view of the camera 620 or in a field of view of a feedback assistance device 618, as described herein, and the system may communicate (e.g., announce) those identified objects. Prior to communicating the objects, object recognition may be performed by analyzing captured images from camera 620. In this regard, the system may continue to analyze captured images to identify the specific object, until, for example, the user requests a different object or stops the search for the specific object (e.g., by providing audible instructions such as "system, stop object search"). Additionally, if the system is not triggered by a received request from the user, the method 200 may simply loop at 202 until a triggering request occurs.

In one embodiment, and not shown at 202, image capturing may be repeatedly occurring at 202, for example in the explore mode, such that one or more images have been captured when a triggering request 202 does occur. In another embodiment, and not shown at 202, in addition to image capturing, object recognition may also be occurring at 204, for example in the explore mode, such that one or more images have been recognized when a triggering request 202 does occur.

If a request is made and the system is triggered, object recognition may be performed by the object recognition engine 204. As mentioned above, object recognition may involve comparing characteristic features within the image to an object identification dataset to identify object matches for a plurality of objects within the image. In the process of making the comparisons, a determination may be made at 206 if known objects have been identified in the image. In this regard, a confidence threshold may be set and only objects that are identified that meet or exceed the confidence threshold may be considered identified objects.

If no known objects are found, the system may provide feedback to the user that no known objects have been identified. A no known objects result may be output to the speech synthesis engine at 208 and the user may be verbally informed that no known objects have been identified in their field of view and the method may return to 202.

If known objects have been identified at 206, a bounding shape (e.g., box) may be defined around the object in the image as provided in a display 612. Further, if known objects are identified, then the names of the objects may be determined, for example, from the object identification dataset, and the speech synthesis engine 208 may be utilized to verbally output the names of the identified objects using text-to-speech. Upon outputting the names of the identified objects, the system may await a user selection at 212 of one of the identified objects by capturing audible information, via the audible input 622 provided by the user. If a selection is not determined, then the system may continue to leverage the speech recognition engine 210 to determine a selection and may request additional information from the user.

Using the speech recognition engine 210, the apparatus 600 may determine the selected object from the user's speech and proceed to highlight the object in the image at 214 to provide a position indication and provide the highlighted image to the user to assist the user with locating the object in the user's field of view. To highlight the image, a variety of image processing filters may be applied in order to enhance or increase the saliency of the selected object in the image while reducing the amount of visual information presented from the background. The bounding shape defined in association with the object recognition may be leveraged for the highlighting process. The type of processing filter used may be a function of a specific user efficacy or preference. According to some example embodiments, a modified variation of the image may be output to the user via a stimulation image that may be sent to a visual prosthesis device such as a retinal or neural prosthesis. In this regard, the stimulation image may include a brighter shape or region in the area of the selected object in the image thereby assisting the user with locating the selected object in their physical surroundings. Upon completion of their interaction with the selected object, the user may quit or complete the request at 216 and return to 202. Alternatively, according to some example embodiments, rather than quit or complete the request at 216, a user may make another selection, for example, using speech recognition at 210 to receive a request for the system to identify all objects in the scene or to receive a request selecting a new object for search. Accordingly, the newly selected object may be highlighted as described above at 214.

Referring now to FIG. 10, which is a block diagram of an example method for object recognition and presentation including aspects of an example search mode as described above and otherwise herein. The example method may be implemented by, for example, the apparatus 600. In this regard, the example method may include, at 700, capturing, by a camera, an image of a field of view of the camera (e.g., camera 16, 404, 620), and, at 702 comparing, by processing circuitry, characteristic features within the image to an object identification dataset to identify object matches for a plurality of objects within the image. The plurality of objects identified in the image may be referred to as the identified objects. The example method may further include, at 704, determining, by the processing circuitry, a name for each identified object from the object identification dataset, and, at 706, determining, by the processing circuitry, locations of the identified objects within the field of view. Further, at 708, the example method may further comprise receiving, by an input device, a user request to communicate the identified objects within in the field of view to the user. At 710, the example method may further include transmitting, by an output device, the name of each identified object in response to receiving the user request, and, at 712, receiving, by an input device, a selected name from the user. The example method may further include, at 714, determining, by the processing circuitry, a selected object based on the selected name. In this regard, the selected object may be one of the identified objects. Additionally, at 716, the example method may include providing, by an assistance feedback device (e.g., assistance feedback device 14, 618) in the form of, for example, a visual prosthesis such as the retinal prosthesis 500 or a neural prosthesis, assistance feedback to the user indicating a position of the selected object within the field of view. In this regard, according to some example embodiments, providing assistance feedback may include, for example, visually highlighting the selected object when the selected object is within the field of view of the assistance feedback device. Alternatively, for example when the selected object is not in the field of view of the assistance feedback device, user cuing may be implemented, as described herein, to indicate to the user a direction to turn the user's head to bring the selected object within the field of view of the assistance feedback device, where such cuing may be implemented using, for example, haptic feedback, spatial sound, visual indications, or the like.

According to some example embodiments, the example method may further include capturing additional images within the field of view, and repeatedly comparing characteristic features within at least some of the additional images to the object identification dataset to identify object matches for the plurality of objects within the image. The example method may further include applying a filter, between iterations of comparing the characteristic features to the object identification dataset, to more than one additional captured image over time to estimate positions of the identified objects based on a prior location determination of the identified objects. The filter may be a Kalman filter that is applied to the more than one captured image.

According to some example embodiments, applying the filter may include performing at least one template match iteration, between iterations of comparing the characteristic features to the object identification dataset, to more than one additional captured image over time to track movement of the objects in the more than one additional captured image. Further, according to some example embodiments, the example method may include capturing the image as a three-dimensional image or filter the image at a target depth. The example method may also include detecting a depth of a target point within the image and outputting a dynamically controlled audible output that is based on a depth of the selected object relative to a depth of the target point. Further, according for some example embodiments, the example method may include using a convolution neural network to compare the characteristic features within the image to an object identification dataset.

The example method may further include receiving the selected name of the object by receiving audible speech from the user and performing speech recognition to determine the name of the selected object. The example method may further comprise providing assistance feedback by rendering a modified version of the image that contrasts the selected object or an area around the selected object with a remainder of the image. According to some example embodiments, the example method may further comprise providing assistance feedback by rendering a modified version of the image with an area around the selected object being cropped to define an object area and a background area. In this regard, the background area may be modified to create contrast. Further, according to some example embodiments, the example method may also comprise providing assistance feedback by rendering a representation of the selected object.

Additionally, based on the foregoing, the processing circuitry 602 may be configured to perform various aspects of the example method of FIG. 10. In this regard, the processing circuitry 602 may be embodied as, include or otherwise control, the apparatus 600 to perform object recognition and presentation including aspects of the search mode as described herein. As such, in some embodiments, the processing circuitry 602 may be said to cause each of the operations described in connection with, for example, the method 100 of FIG. 11, the method 200 of FIG. 9, the method of FIG. 10, and the functionalities otherwise described herein. The processing circuitry 602 may therefore undertake the corresponding functionalities responsive to execution of instructions or algorithms configuring the processing circuitry 602 accordingly. The processing circuitry 602 may provide programmable control signals, selections, and the like to control the operation of the apparatus 600 responsive to execution of instructions stored in the memory 604.

As such, according to some example embodiments, the processing circuitry 602 may be configured to receive an image from the camera 620. The processing circuitry 602 may also be configured to compare characteristic features within the image to an object identification dataset (e.g., stored in the memory 604) to identify object matches for a plurality of objects within the image. The plurality of objects identified in the image may be referred to as identified objects. The processing circuitry 602 may also be configured to determine a name for each identified object from the object identification dataset, and determine locations of the identified objects within the field of view. The processing circuitry 602 may be configured to receive a user request via the user interface 608, or more specifically an input device operably coupled to the user interface 608, to communicate the identified objects within in the field of view to the user, and transmit, via the user interface 608, the name of each identified object in response to receiving the user request. Further, the processing circuitry 602 may be configured to receive a selected name from the user via, for example, an input device, and determine a selected object based on the selected name. The selected object may be one of the identified objects. The processing circuitry 602, via the assistance feedback device 618, may also transmit assistance feedback to the user indicating a position of the selected object within the field of view via the assistance feedback device 618.

According to some example embodiments, the processing circuitry 602 may also be configured to capture additional images within the field of view of camera 620, and repeatedly compare characteristic features within at least some of the additional images to the object identification dataset to identify object matches for the plurality of objects within the image. Further, the processing circuitry 602 may be configured to apply a filter, between iterations of comparing the characteristic features to the object identification dataset, to more than one additional captured image over time to estimate positions of the identified objects based on a prior location determination of the identified objects. The filter may be a Kalman filter applied to the more than one captured image. Further, the processing circuitry 602 may also be configured to perform at least one template match iteration, between iterations of comparing the characteristic features to the object identification dataset, to more than one additional captured image over time to track movement of the objects in the more than one additional captured image.

According to some example embodiments, the processing circuitry 602 may be configured to cause the camera 620 to capture the image as a three-dimensional image. In this regards, according to some example embodiments, the processing circuitry 602 may be further configured to filter the image at a target depth. Additionally, the processing circuitry 602 may be configured to detect a depth of a target point within the image (e.g., a centroid of a selected object) and output a dynamically controlled audible output that is based on a depth of the selected object relative to a depth of the target point.

The processing circuitry 602 may also be configured to utilize a convolution neural network to compare the characteristic features within the image to an object identification dataset. According to some example embodiments, the processing circuitry 602 may receive, via the user interface 608, audible speech from the user and perform speech recognition to determine the name of the selected object. According to some example embodiments, the processing circuitry 602 may be configured to provide assistance feedback by rendering a modified version of the image (e.g., via the assistance feedback device 618) that contrasts the selected object or an area around the selected object with a remainder of the image. Further, according to some example embodiments, the processing circuitry 602 may be configured to render, via the assistance feedback device 618, a modified version of the image with an area around the selected object being cropped to define an object area and a background area. For example, the background area may be modified to create contrast with the selected object, by, for example, darkening, disabling, or nullifying the pixels of the background area. The processing circuitry 602 may be further configured to, according to some example embodiments, provide assistance feedback by rendering, via the assistance feedback device 618, a representation of the selected object. The processing circuitry 602 may be further configured to, according to some example embodiments, provide assistance feedback in the form of audible cueing, via an output device, to indicate a direction that the user should move to interface with the selected object. In this regard, the processing circuitry 602 may be configured to cue the user move, for example, their head to reposition the camera 620 to be centered at the selected object or move their hand in the captured image in a direction to engage the selected object. For example, the assistance feedback may be verbal cues from an output device indicated that the user should, for example, move their hand to the left. Additionally, the processing circuitry 602 may be configured to support visual cuing in the event that a selected object moves out of the field of view. In this regard, the processing circuitry 620 may be configured to analyze the captured images and determine a location of the selected object relative to a point (e.g., the center) of the field of view. The processing circuitry 620 may be configured to transmit assistance feedback in the form of a modified image that includes an indicator of where the user should move the field of view to bring the selected object back into the field of view. According to some example embodiments, the indicator may be a bright area at or near an edge of the modified image closest to a determined position of the selected object.

Now referring to FIG. 11, an example method 100 is illustrated as an example interaction between a user and an object recognition and presentation system (e.g., apparatus 600) to improve a visually impaired individual's ability to interact with objects in their environment via aspects of a search mode. To implement the example method 100, image capturing, audio output, audio input and feedback assistance devices may be involved. Further, processing circuitry for image analysis, speech synthesis, speech recognition, and presentation of feedback may also be utilized.

In the regard, the method 100 may begin with a scenario where a visually impaired individual may wish to locate and drink from a mug at 102. At 104, an image of objects on a table in front of the individual may be captured, for example by a camera 620, for example, affixed to the individual's glasses, and, since the scene is unknown, the captured image may be analyzed to identify at least some of the objects within the image. A variety of image analysis techniques can be used, according to various example embodiments, to identify the objects including algorithms that leverage machine learning and, for example, convolutional neural networks (CNNs) to identify the objects. In general, according to some example embodiments, a comparison of characteristic features within an image may be performed against an object identification dataset to identify object matches for a plurality of objects within the image. As shown at 104, for example, such a comparison has been performed and a calculator, a pen, and a mug have been identified.

Upon identifying objects within the captured image or images, the method 100 may continue by determining a name for each of the identified objects by leveraging, for example, nomenclature information associated or integrated with the object identification dataset. At 106, speech synthesis may be performed to prepare the determined names for output to the user as audible speech via an audible output device at 108. As shown, for example, the words "calculator," "pen," and "mug" may be spoken using speech synthesis.

At 110, the user may respond with a verbal selection of an identified object. In this example scenario, the user may speak "mug" to make the selection. At 112, an audio input 622 may receive the user's speech selection of "mug" and perform a speech recognition analysis on the received speech at 114 to determine which identified object the user has selected.

Upon determining that the user has selected the mug, an image modification operation may be performed at 116 to filter or highlight the selected object in the captured image. According to some example embodiments, a portion of the image associated with or surrounding the selected object may be isolated or cropped and contrasted with the remainder of the image to highlight the selected object and more clearly reveal to the visually impaired user where, in the user's field of view, the selected object is located. In this regard, it can be seen at 116 that a portion of the image associated with the mug has been isolated and contrasted to more clearly present both the mug and its position in the field of view to the user. At 116, the modified image may be provided or displayed to the user for example, via communications with a visual prosthesis.

According to some example embodiments, a further modification to the captured image may be generated in the form of a stimulation output to a visual prosthesis at 118 (e.g., a retinal or neural prosthesis). In this regard, rather than, or in addition to, cropping and filtering (e.g., downsampling) the image with respect to the selected object, the image may be modified such that a position indication as a visual representation of the position of the selected object within the field of view is provided. Such visual representation may be indicative of the data that may be transmitted to a visual prosthesis for stimulation. The visual representation may be shaped or colored in a manner that makes the representation readily discernable by an individual that is visually impaired.

With the position indication or information provided as feedback to the user, the user may understand where in their surroundings an object of interest is located, based on the highlighted position of the object in the field of view. The user may then proceed to interact with the object, which, in this example scenario, may involve picking up the mug and taking a sip of coffee, for example.

As introduced above, and further described in the following, the apparatus 600 and the processing circuitry 602 may be configured to perform cuing to assist a user with locating a position of a desired object, typically in association with the search mode. In this regard, cuing may be the process of communicating to a user which direction to move the assistance feedback device 618 to bring a desired object into the field of view of the assistance feedback device 618. As such, cuing may be used for identified objects that are in the field of view of the assistance feedback device 618 but, for example, are not centered in the field of view of the assistance feedback device 618. Additionally, cuing may be used for identified objects that are not in the field of view of the assistance feedback device 618 but are in the field of view of the camera 620. Cuing may also be used for identified objects that are not in the field of view of the assistance feedback device 618 and are not in the field of view of the camera 620, but the position of the desired object has been stored and therefore can be used for cuing purposes.

Generally, according to some example embodiments, to perform cuing, the processing circuitry 602 may be configured to output a cuing prompt to the user in association with a selected identified object. In this regard, the cuing prompt may provide an indication of a direction for the user to move the assistance feedback device field of view relative to the position of the selected identified object. The cuing prompt may be provided in a variety of ways including audibly, visually, or via haptic feedback. As an audible prompt, the cuing prompt may be provided as synthesized speech indicating a direction, e.g., "right," "left," "up," "down" or the like or by generating spatial sound that is perceived by the user to emanate from the direction of the target object. As visual feedback, a border region of the field of view of the assistance feedback device 618 may be highlighted or blinked, for example, to prompt the user to turn their head in the direction of the highlighted border region. As haptic feedback, the cuing prompt may be a haptic vibration that is provided as an encoded signal to indicate a desired direction of movement. For example, a long vibration (e.g., a dash) may indicate that a movement to the right is desired, a short burst vibration (e.g., a dot) may indicate that a movement to the left is desired. As such, various haptic signal patterns may be used to provide cuing. Or haptic feedback for cuing may be implemented using multiple haptic actuators, such as by arranging the actuators in a geometric pattern, for example, on a hand pad or a on a head-mounted device to signify a specific direction by selectively activating one or more of the haptic actuators associated with the direction of the target object. Further, according to some example embodiments, the cuing prompt may include a dynamic frequency characteristic (e.g., a tone or vibration with a changing frequency) indicative of a distance from a point in the assistance feedback device field of view to the position of the selected identified objects. In this regard, the cuing prompt may, for example, increase in audible or vibration frequency as the field of view of the assistance feedback device 618 moves closer to the selected identified object being within the field of view or central to the field of view.

As mentioned above, when the selected, identified object is outside of the field of view of the camera, a previously stored position of the selected, identified object may be used to provide cuing. To store the positions of identified objects, the processing circuitry 602 may be configured to track movement of the camera 620 to determine camera movement data, determine positions of identified objects based on the camera movement data, and store position data describing the positions of identified objects, for example, in the memory 604 for later retrieval. As such, via the camera movement data being currently provided, a direction and distance to the position of the previously identified object can be determined.

With reference to FIGS. 12 and 13, an example cuing scenario is provided in accordance various example embodiments. In this regard, referring specifically to FIG. 12, the user has requested to locate a cup. As shown in FIG. 12, the cup is within the camera field of view 1200, but outside of the field of view of the assistance feedback device 618. As such, the stimulation pattern 1204 is blank, therefore providing no direction information to the user. However, if cuing is implemented, the processing circuitry 602 may identify the position of the cup, either within the images or via a stored position, and provide a cuing prompt based on the same. In this regard, since the cup is located to the right of the assistance feedback device 618 field of view, the apparatus 600 may audibly output through voice synthesis "RIGHT" at 1206 to indicate that the user should move the assistance feedback device 618's field of view to the right. Such cuing may be, for example, repeated until the cup appears in the stimulation pattern 1204 or is located central to the stimulation pattern.

In this regard, FIG. 13 shows the cup being located. The user has moved her head (and thus the camera 620 and the assistance feedback device 618) into a position, in response to the cuing, where the cup is now centrally located within the stimulation pattern 1304. With cup now centrally located within the field of view of the assistance feedback device 618, the processing circuitry 602 may be configured to discontinue cuing and a position indication for the cup is provided at 1304. Further, at 1306, the apparatus 600 may be configured to audibly output "Cup Located" in response to the field of view for the assistance feedback device 618 being moved such that the cup covers a central point of the assistance feedback device 618 field of view.

As used herein, the term "module" is intended to include a computer-related entity, such as but not limited to hardware, software, or a combination of hardware and software. For example, a module may be, but is not limited to being a software or hardware implementation of a process, an object, an executable, and/or a thread of execution, which may be implemented via a processor or computer. By way of example, both an application running on a computing device and/or the computing device can be a module. One or more modules can reside within a process and/or thread of execution and a module may be localized on one computer and/or distributed between two or more computers. In addition, these modules can execute from various computer readable media having various data structures stored thereon. The modules may communicate by way of local and/or remote processes such as in accordance with a signal having one or more data packets, such as data from one module interacting with another module in a local system, distributed system, and/or across a network such as the Internet with other systems by way of the signal. Each respective module may perform one or more functions that will be described in greater detail herein. However, it should be appreciated that although such example is described in terms of separate modules corresponding to various functions performed, some examples need not necessarily utilize modular architectures for employment of the respective different functions. Thus, for example, code may be shared between different modules, or the processing circuitry itself may be configured to perform all of the functions described as being associated with the modules described herein. Furthermore, in the context of this disclosure, the term "module" should not be understood as a nonce word to identify any generic means for performing functionalities of the respective modules. Instead, the term "module" should be understood to be a modular entity that is specifically configured in, or can be operably coupled to, processing circuitry to modify the behavior and/or capability of the processing circuitry based on the hardware and/or software that is added to or otherwise operably coupled to the processing circuitry to configure the processing circuitry accordingly.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements or functions, it should be appreciated that different combinations of elements or functions may be provided by alternative embodiments without departing from the scope of the appended claims. In this regard, for example, different combinations of elements or functions than those explicitly described above are also contemplated as may be set forth in some of the appended claims. In cases where advantages, benefits or solutions to problems are described herein, it should be appreciated that such advantages, benefits or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed is:

1. An apparatus configured to perform object recognition, the apparatus comprising:
 a camera configured to capture a plurality of images and to transmit the plurality of images to processing circuitry;
 an assistance feedback device having a field of view that is positionable by a user, the assistance feedback device being in communication with the processing circuitry, the assistance feedback device field of view corresponding to a current camera position; and
 the processing circuitry configured to:
  receive the plurality of images from the camera;
  repeatedly determine characteristic features within the plurality of images and compare the characteristic features within the plurality of images to an object identification dataset to determine object matches for identified objects within the plurality of images;
  determine a name for identified objects from the object identification dataset;
  output, using the assistance feedback device, a position indicator for identified objects; and
  output the name of identified objects within the assistance feedback device field of view.

2. The apparatus of claim 1 further comprising a user input device in communication with the processing circuitry;
 wherein the processing circuitry is further configured to receive an object category selection from a user input device; and
 wherein the object matches for identified objects satisfy the object category selection.

3. The apparatus of claim 1 further comprising a user context sensor configured to output user context information to the processing circuitry;
 wherein the processing circuitry is further configured to:
  receive the user context information from the user context sensor;
  determine an object category selection based on the user context information; and
  determine object matches for identified objects within the object category selection.

4. The apparatus of claim 1, further comprising a user context sensor configured to output user context information to the processing circuitry;
 wherein the processing circuitry is further configured to:
  receive the user context information from the user context sensor; and
  determine an object category selection based on the user context information; and
 wherein the processing circuitry is configured to compare the characteristic features within the plurality of images to the object identification dataset, the object identification dataset being reduced or expanded based on the object category selection to determine the object matches for the identified objects.

5. The apparatus of claim 4 wherein the user context sensor is a location sensor configured to output location information as user context information.

6. The apparatus of claim 1, wherein the processing circuitry is further configured to output the name of identified objects via an audible output or a refreshable braille display.

7. The apparatus of claim 1 wherein the processing circuitry is further configured to: track movement of the camera to determine camera movement data;
 determine positions of identified objects based on the camera movement data; and
 store position data describing the positions of identified objects.

8. The apparatus of claim 7, wherein the processing circuitry is further configured to output a cuing prompt to the user in association with a selected one of the identified objects, the cuing prompt indicating a direction for the user to move the assistance feedback device field of view with respect to the position of the selected one of the identified objects, wherein the position of the selected one of the identified objects is determined based on the stored position data.

9. The apparatus of claim 1, wherein the processing circuitry is further configured to output a cuing prompt to the user in association with a selected one of the identified objects, the cuing prompt indicating a direction for the user to move the assistance feedback device field of view with respect to the position of the selected one of the identified objects, wherein the position of the selected one of the identified objects is within the assistance feedback device field of view or outside of the assistance feedback device field of view.

10. The apparatus of claim 1, wherein the processing circuitry is further configured to output a cuing prompt to the user in association with a selected one of the identified objects, the cuing prompt indicating a direction for the user to move the assistance feedback device field of view with respect to the position of the selected one of the identified objects, the cuing prompt including a dynamic frequency characteristic indicative of a distance from a point in the assistance feedback device field of view to the position of the selected one of the identified objects.

11. The apparatus of claim 1, wherein the processing circuitry is further configured to output a cuing prompt to the user in association with a selected one of the identified objects, the cuing prompt indicating a direction for the user to move the assistance feedback device field of view with respect to the position of the selected one of the identified objects, the cuing prompt comprising a haptic output, audible output, or visual output.

12. A system for performing object recognition, the system comprising:
   an assistance feedback device comprising a visual prosthesis, the assistance feedback device having a field of view that is positionable via movement of a user;
   a remote apparatus comprising:
      a camera configured to capture a plurality of images; and
      processing circuitry configured to:
         receive the plurality of images from the camera;
         repeatedly determine characteristic features within the plurality of images and compare the characteristic features within the plurality of images to an object identification dataset to determine object matches for identified objects within the plurality of images;
         determine a name for identified objects from the object identification dataset;
         output, using the assistance feedback device, a position indicator for identified objects to the user; and
         output the name of identified objects within the assistance feedback device field of view.

13. The system of claim 12, wherein the remote apparatus further comprises a user input device in communication with the processing circuitry;
   wherein the processing circuitry is further configured to receive an object category selection from a user input device; and
   wherein the processing circuitry is configured to determine object matches for identified objects, the identified objects satisfying the object category selection.

14. The system of claim 12 further comprising a user context sensor configured to output user context information to the processing circuitry;
   wherein the processing circuitry is further configured to:
      receive the user context information from the user context sensor; and
      determine an object category selection based on the user context information; and
   wherein the processing circuitry is configured to determine object matches for identified objects, the identified objects satisfying the object category selection.

15. The system of claim 12 wherein the processing circuitry is further configured to: track movement of the camera to determine camera movement data;
   determine positions of identified objects based on the camera movement data; and
   store position data describing the positions of identified objects.

16. The system of claim 15, wherein the processing circuitry is further configured to output a cuing prompt to the user in association with a selected one of the identified objects, the cuing prompt indicating a direction for the user to move the assistance feedback device field of view with respect to the position of the selected one of the identified objects, wherein the position of the selected one of the identified objects is determined based on the stored position data.

17. The system of claim 12, wherein the processing circuitry is further configured to output a cuing prompt to the user in association with a selected one of the identified objects, the cuing prompt indicating a direction for the user to move the assistance feedback device field of view with respect to the position of the selected one of the identified objects, wherein the position of the selected one of the identified objects is within the assistance feedback device field of view or outside of the assistance feedback device field of view.

* * * * *